US006998516B2

(12) United States Patent
Brar et al.

(10) Patent No.: US 6,998,516 B2
(45) Date of Patent: Feb. 14, 2006

(54) TRANSFORMATION AND REGENERATION OF SUNFLOWER COTYLEDONS

(75) Inventors: Gurdip S Brar, Middleton, WI (US); Gail A Roberts, Madison, WI (US)

(73) Assignee: Monsanto Technology LLC, St. Louis, MO (US)

( * ) Notice: Subject to any disclaimer, the term of this patent is extended or adjusted under 35 U.S.C. 154(b) by 511 days.

(21) Appl. No.: 09/683,765

(22) Filed: Feb. 12, 2002

(65) Prior Publication Data

US 2002/0157138 A1 Oct. 24, 2002

Related U.S. Application Data

(60) Provisional application No. 60/268,209, filed on Feb. 12, 2001.

(51) Int. Cl.
*A01H 1/00* (2006.01)
*A01H 5/00* (2006.01)
*C12N 15/82* (2006.01)
*C12N 15/87* (2006.01)

(52) U.S. Cl. ....................... 800/278; 800/294; 800/322

(58) Field of Classification Search ................ 800/322, 800/294

See application file for complete search history.

(56) References Cited

U.S. PATENT DOCUMENTS 6,130,368 A 10/2000 Londesborough et al.

OTHER PUBLICATIONS

Hansen et. al., 1999, Trends in plant Science, vol. 4, pp. 226-231, see p. 230.*

Ceriani, M.F. et al, "Cotyledons: an explant for routine regeneration of sunflower plants," Plant Cell Physiol., vol. 33 (2), p. 157-164, (1992).

Coca, M.A. et al, "Differential regulation of small heat shock genes in plants: analysis of a water stress inducible and developmentally activated sunflower promoter," Plant Mol. Biol., vol. 31, p. 863-876, (1996).

Goffner, D. et al, "Effects of abscisic acid and osmotica on Helianthinin gene expression in sunflower cotyledons in vitro," Plant Sci., vol. 66, p. 211-219, (1990).

Grayburn, W.S. et al, "Transformation of sunflower (*Helianthus annuus* L.) following wounding with glass beads," Plant Cell Reports, vol. 14, p. 285-289, (1995).

Hammond, R.W, "Agrobacterium mediated inoculation of PSTVd cDNAs onto tomato reveals the biological effect of apparently lethal mutations," Virology, vol. 201, p. 36-45, (1994).

Kutschera, U. et al, "Cell elongation, turgor and osmotic pressure in developing sunflower hypocotyls," J. Exp. Botany, vol. 45 (No. 274), p. 591-595, (1994).

Kutschera, U, "Cell expansion in plant development," Revista Brasileira de Fisiologia Vegetal, vol. 12 (1), p. 65-95, (Apr. 2000).

Kutschera, U, "Role of the cotyledons in the maintenance of hypocotyl growth in *Helianthus annuus* L., " Plant Physiol., vol. 140, p. 319-323, (1992).

Laparra, H. et al, "Expression of foreign genes in sunflower (*Helianthus annuus* L.): evaluation of three gene transfer methods," Euphytica, vol. 85, p. 63-74, (1995).

McNeil, D.L., "The basis of osmotic pressure maintenance during expansion growth in *Helianthus annuus* hypocotyls," Aust. J. Plant Physiol., vol. 3 (3), p. 311-324, (1976).

Pfeiffer, I. et al, "Sucrose metabolism and lipid mobilization during light induced expansion of sunflower cotyledons," J. Plant Physiol., vol. 147, p. 553-558, (1996).

Rao, K.S. et al, "Agrobacterium mediated transformation of sunflower (*Helianthus annuus* L.): a simple protocol," Annals of Botany, vol. 83, p. 347-354, (1999).

Xu, Y. et al, "Transfer and expression of the T-DNA haboured by Agrobacterium tumefaciens in cultured explants *Helianthus annuus*," Acta Bio. Yunnanica, vol. 10(1), p. 159-166, (1988).

* cited by examiner

*Primary Examiner*—Elizabeth McElmain
*Assistant Examiner*—Georgia Helmer
(74) *Attorney, Agent, or Firm*—M. Todd Rands

(57) ABSTRACT

The present invention relates to improved methods for producing transgenic sunflower plants. Specifically, methods are disclosed for transforming sunflower tissues and regenerating fertile transgenic plants therefrom. The methods are particularly amenable to sunflower tissues, such as cotyledons, which have proven refractory to previous methods of transformation and regeneration.

20 Claims, 12 Drawing Sheets

TRANSFORMATION AND REGENERATION OF SUNFLOWER COTYLEDONS

This application claims priority to U.S. Provisional Application No. 60/268,209 filed Feb. 12, 2001, herein incorporated by reference in its entirety.

BACKGROUND OF INVENTION

The present invention relates to methods of producing transgenic sunflower (*Helianthus annuus* L.) plants. Specifically, methods for *Agrobacterium*-mediated transformation of sunflower cotyledon cells, induction of transgenic shoots, and regeneration of fertile transgenic sunflower plants are disclosed.

The expanding field of biotechnology provides the tools for scientists to introduce important traits into a variety of plant species. New technologies make possible the production of commercially viable transgenic crops having significant economic impact on the agricultural industry. These advancements enable the creation of new crop germplasm containing novel traits. Such traits include improvements in the nutritional quality, insect resistance, disease resistance, and yield of many crops. Sunflower (*Helianthus annuus* L.) is one of the world's most important oil crops. Accordingly, much effort is continually directed toward the genetic engineering of this agronomically important crop species.

Genetic engineering of plants is essentially a two-step process: transformation and regeneration. First, plant cells are transformed, thereby introducing a nucleic acid sequence, which is typically integrated into the genome of the host cell. Second, a sexually competent plant is regenerated from the transformed cells. The transformation and regeneration processes preferably are complementary such that successfully transformed tissues are further capable of developing into competent whole plants.

Several methods, well known in the art, are available for introducing DNA into plant cells. Suitable methods include, but are not limited to, bacterial infection, binary bacterial artificial chromosome vectors, and direct delivery of DNA, e.g., via PEG-mediated transformation, desiccation/inhibition-mediated DNA uptake, electroporation, agitation with silicon carbide fibers, and acceleration of DNA coated particles (reviewed in Potrykus, *Ann. Rev. Plant Physiol. Plant Mol. Biol.,* 42: 205, 1991).

Many plants, including several important crop species, have been transformed using an *Agrobacterium tumefaciens* mediated transformation methodology. *Agrobacterium*-mediated transformation of sunflower has also been reported (Schrammeijer et al., *Plant Cell Reports,* 9: 55–60, 1990; EP 0 486 234). Transformed tissues reportedly included hypocotyls, apical meristems, and protoplasm.

*Agrobacterium*-mediated transformation of sunflower cotyledons has also been attempted. Utilizing cotyledons affords several advantages that other plant tissues do not. For instance, unlike many plant explants, minimal manipulation is required to prepare cotyledons for the transformation and regeneration processes. Also, source tissue is readily available in the form of mature seeds. In addition, cotyledons have demonstrated high potential for plant regeneration in several plant species (Sharma et al., *Plant Sci.,* 66: 247–254, 1990; Mante et al., *In Vitro Cell Dev. Biol.,* 25: 385–388, 1989). Furthermore, cotyledons can often give rise to shoots without an intervening callus stage. As a result, whole plants are obtained more rapidly and efficiently (Knittel etal., *Plant Science,* 73: 219–226, 1991).

Unfortunately, sunflower cotyledons have proven largely refractory to *Agrobacterium*-mediated transformation. Many of these attempts require extensive preparation of the cotyledons or additional equipment (such as a particle gun). Furthermore, in the few instances where successful transformation is reported, the transformed cotyledons have generally not been competent for induction of transgenic shoots. In some instances, chimeric shoots have been reported. However, there have not been reports to date of successful transformation of sunflower cotyledons with subsequent regeneration of fertile transgenic sunflower plants.

Ceriani et al. (*Plant Cell Physiol.* 33(2): 157–164, 1992) report the susceptibility of sunflower cotyledons to *Agrobacterium tumefaciens* infection. A low frequency of tumor-like growths is reported on the cotyledons after co-culture with *Agrobacterium tumefaciens*. Ceriani does not, however, attempt to initiate shoot formation or regenerate plants from the reported *Agrobacterium*-infected cotyledons.

Baker et al. (*In Vitro Cell Dev.* 31(3): 68A, 1995) describe the transformation of tissue explants from sunflower, including cotyledons, using micro-particles coated with *Agrobacterium tumefaciens*. The *Agrobacterium* is dried onto the micro-particles in a manner that maintains the viability of the bacteria. The explants treated according to this method reportedly formed chimeric shoots containing positively transformed regions.

Laparra et al. (*Euphytica.* 85: 63–74, 1995) describe transformation of several sunflower tissues, including cotyledon explants, via direct gene transfer, particle bombardment, and *Agrobacterium* infection. Regions of cotyledons were reportedly transformed by *Agrobacterium* infection. These transformed cotyledons, however, were incapable of regenerating into transgenic shoots. Laparra explains that "transformation occurs in the region, but not the cell type, competent for shoot regeneration." Conversely, when a correct cell type was successfully transformed, this transformed region was ill suited to the regeneration of transgenic shoots.

Clearly, there is a need in the art for improved methods of producing transgenic sunflower plants via transformation and regeneration of sunflower cotyledon tissue.

SUMMARY OF INVENTION

The present invention relates to improved methods for producing transgenic sunflower plants. Specifically, methods are disclosed for transforming sunflower tissues and regenerating fertile transgenic plants therefrom. The methods are particularly amenable to sunflower tissues, such as cotyledons, that have proven refractory to previous methods of transformation and regeneration.

In addition to the advantages related to the use of cotyledons as described above, further improvements realized in the practice of the present invention include higher transformation frequencies; minimal manipulation and handling of the plant tissues; shorter time required to obtain regenerated plants; clonal origin of the regenerated plants; and better reproducibility.

In a preferred embodiment, the invention comprises novel compositions of media and culture conditions for use at particular stages of transformation and regeneration. In one preferred embodiment it has been discovered that a method for sunflower cotyledon transformation utilizing media in the inoculation/co-culture and delay stages of transformation that contains relatively high osmoticum levels and then reducing the osmoticum level in the shoot induction and delay media enables the use of sunflower cotyledons as the explant for sunflower transformation. Furthermore, it has been observed that improvements to the transformation of sunflower cotyledons may be obtained by treating the cotyledons at about 4° C. for about 24 hours prior to infection with *Agrobacterium*. Moreover, a selection mechanism involving three selection media containing varying concentrations of the selective agent provides improved selection of transformed sunflower tissue. The overall process may be briefly summarized as follows.

Preparation of Sunflower Tissue

Sunflower seeds are typically sterilized and germinated. Germinated seedlings may then be incubated in the cold. Prior to transformation, the cold-treated seedlings may be processed by cutting, tearing, slicing, breaking, or otherwise manipulating the plant tissues. If cotyledons are to be transformed, they may be broken or cut along the root-shoot axis.

Infiltration and Delay Cultures

*Agrobacterium* is typically prepared according to standard protocols. The *Agrobacterium* typically contains at least one nucleic acid sequence of interest and/or a nucleic acid sequence encoding a selectable marker. The cotyledon pieces can be inoculated with the *Agrobacterium* in an infiltration/co-culture medium.

After co-culture with the *Agrobacterium*, the inoculated tissue may be transferred to a delay medium. The delay media is generally designed to limit the growth of *Agrobacterium* without using a selective agent, while permitting any transformed cells to continue growing.

The infiltration/co-culture media and the delay media preferably have a high osmotic pressure (or osmoticum concentration) and no antibiotics. The osmotic pressure of the delay media is most preferably between about 200 mOsm and about 750 mOsm. This high osmolarity may be provided by any compatible solute including, but not limited to, organic salts, inorganic salts, and carbohydrates. The solute preferably is a carbohydrate, such as glucose, sucrose, fructose, maltose, mannose, mannitol, or xylose, and most preferably is sucrose. The optimal concentration of the carbohydrate in the delay media is more preferably between about 9% (w/v) and about 15% (w/v), and most preferably 12% (w/v) to provide the high osmoticum.

Selection of Transformed Cells and Induction of Transgenic Shoots

After incubation in the delay media, the cotyledons are preferably placed in a culture containing selection media. Typically, the selection media contains an antibiotic. A percentage of the positively transformed cells generally survive the selection. The transformed tissue is preferably incubated sequentially under three different selection media. The first and third selection media contain a low concentration of selective agent. The second media contains a high concentration of selective agent. Thus, the selection is sequentially carried out with low-high-low selective pressure. The selection media also has an osmoticum concentration of between about 1% to about 3%, and more preferably about 1%. While being cultured in the selection media, the transformed cotyledons are monitored for the formation of transgenic shoots.

Elongation Culture and Regeneration of Transgenic Plants

As transgenic shoots develop, they are transferred to an elongation culture. The conditions and media compositions suitable for the elongation are well know to those in the art and will typically include a low osmoticum concentration similar to that in the selection media.

After a period of elongation, the elongated shoots are typically either rooted or grafted on to non-transgenic or transgenic sunflower plants. As scions develop, they may be grafted onto stock plants and transferred to a greenhouse. This R(0) generation is allowed to grow, develop, flower, and produce seeds. Alternatively, the shoots may be directly rooted on rooting media and allowed to grow, develop, flower, and produce seeds. In either case, the seeds may be tested to confirm the presence of the nucleic acid sequence transferred by the *Agrobacterium*. The seeds may then be used to produce subsequent generations of transgenic plants.

DETAILED DESCRIPTION

Figure 1:
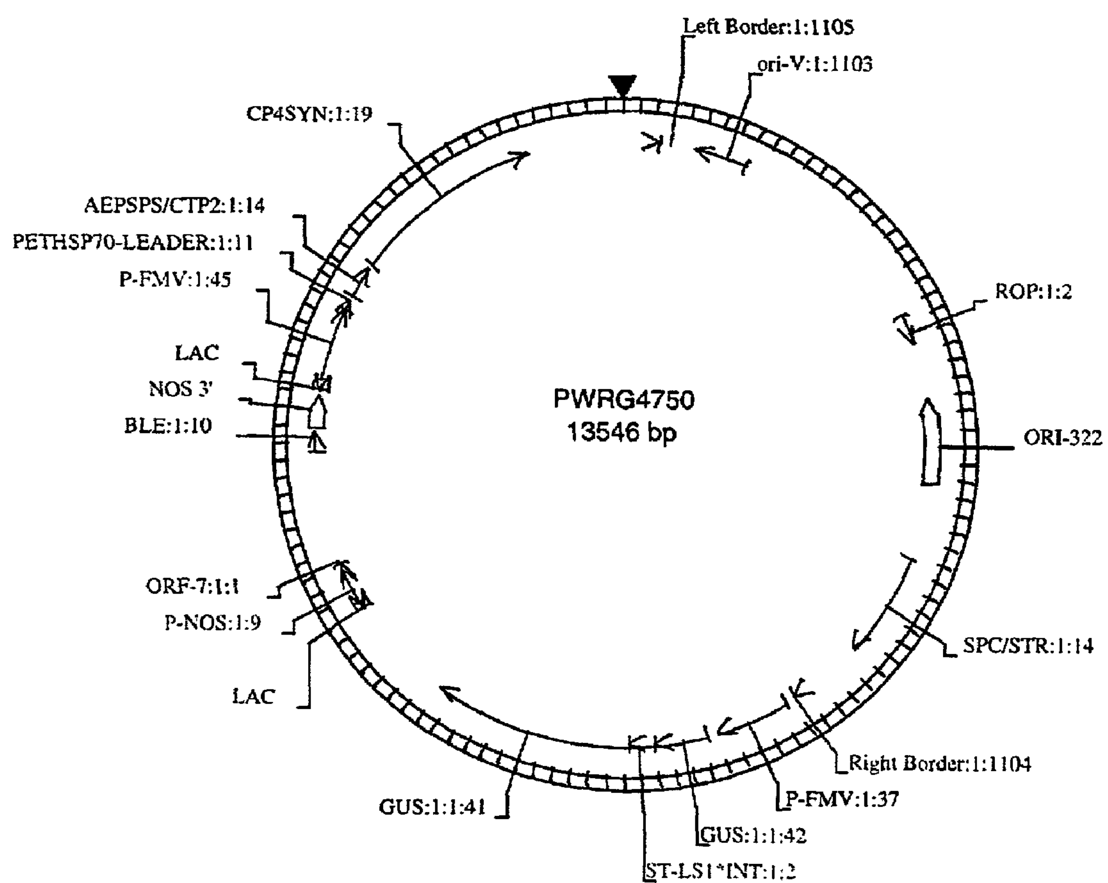
FIG. 1 is a representation of a plasmid map of pWRG4750.
Figure 2:
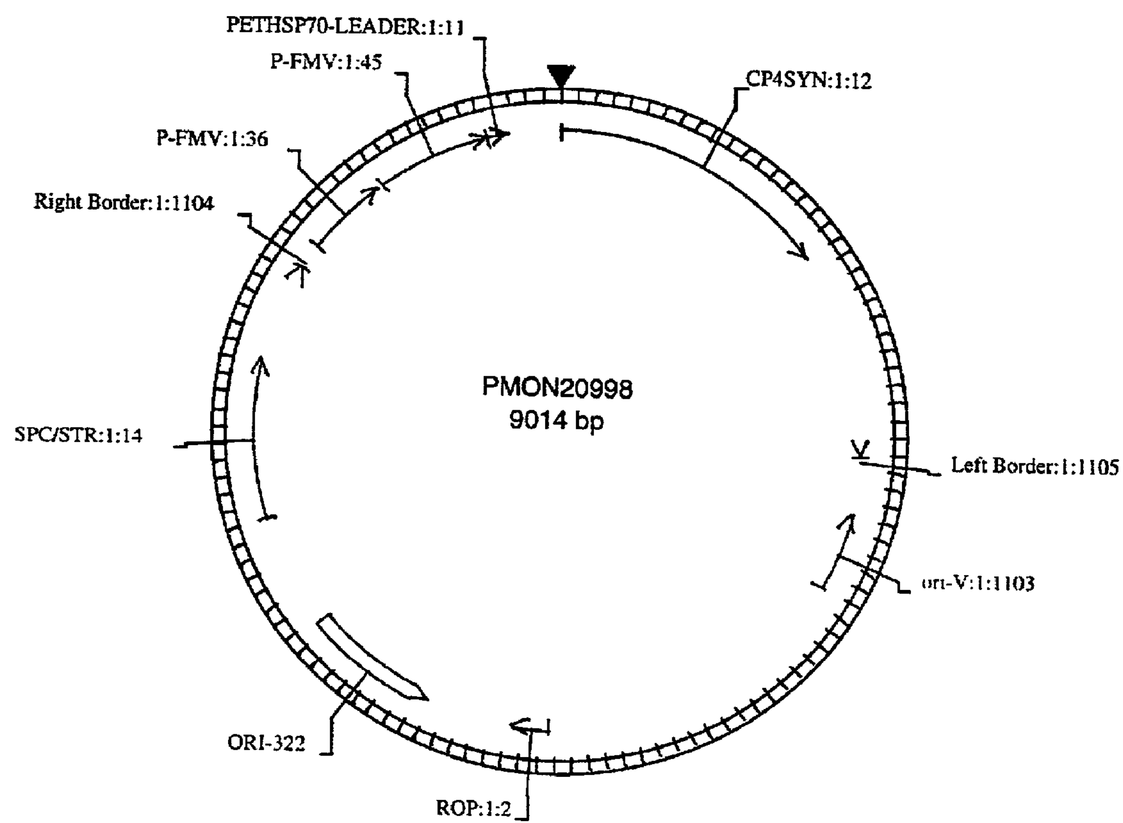
FIG. 2 is a representation of a plasmid map of pMON20998.
Figure 3:
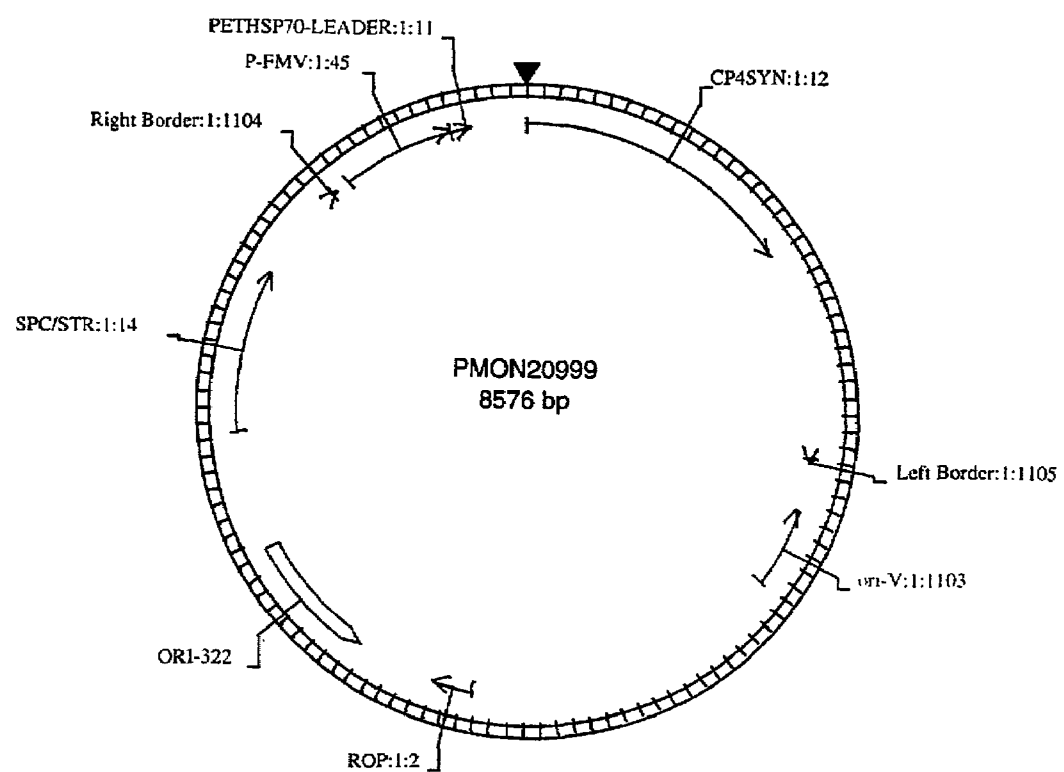
FIG. 3 is a representation of a plasmid map of pMON20999.
Figure 4:
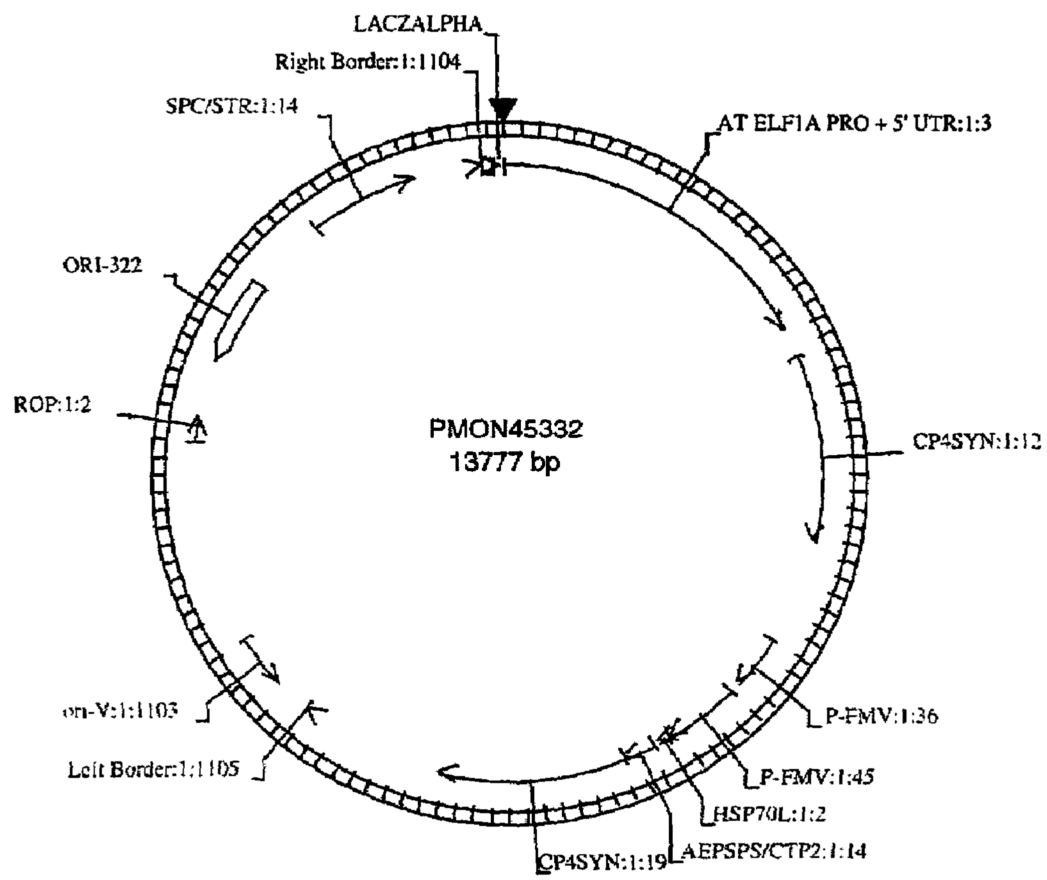
FIG. 4 is a representation of a plasmid map of pMON45332.
Figure 5:
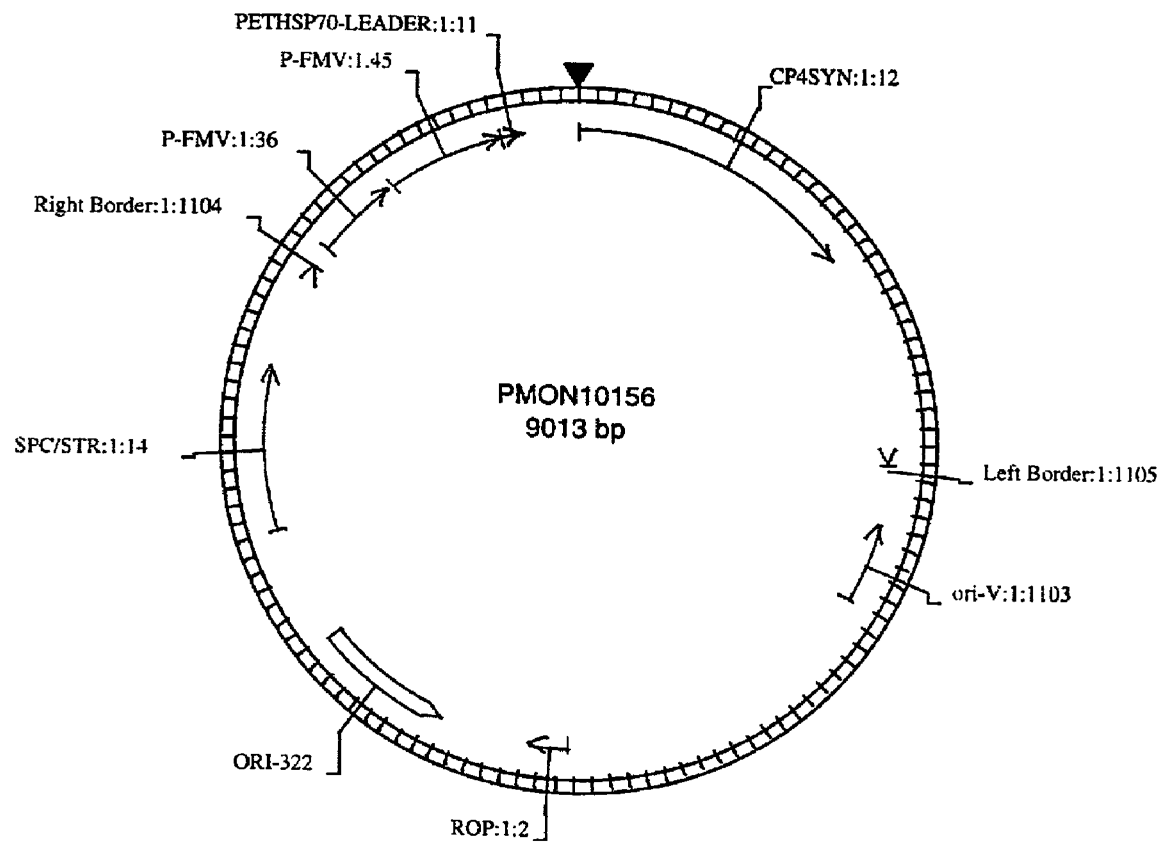
FIG. 5 is a representation of a plasmid map of pMON10156.
Figure 6:
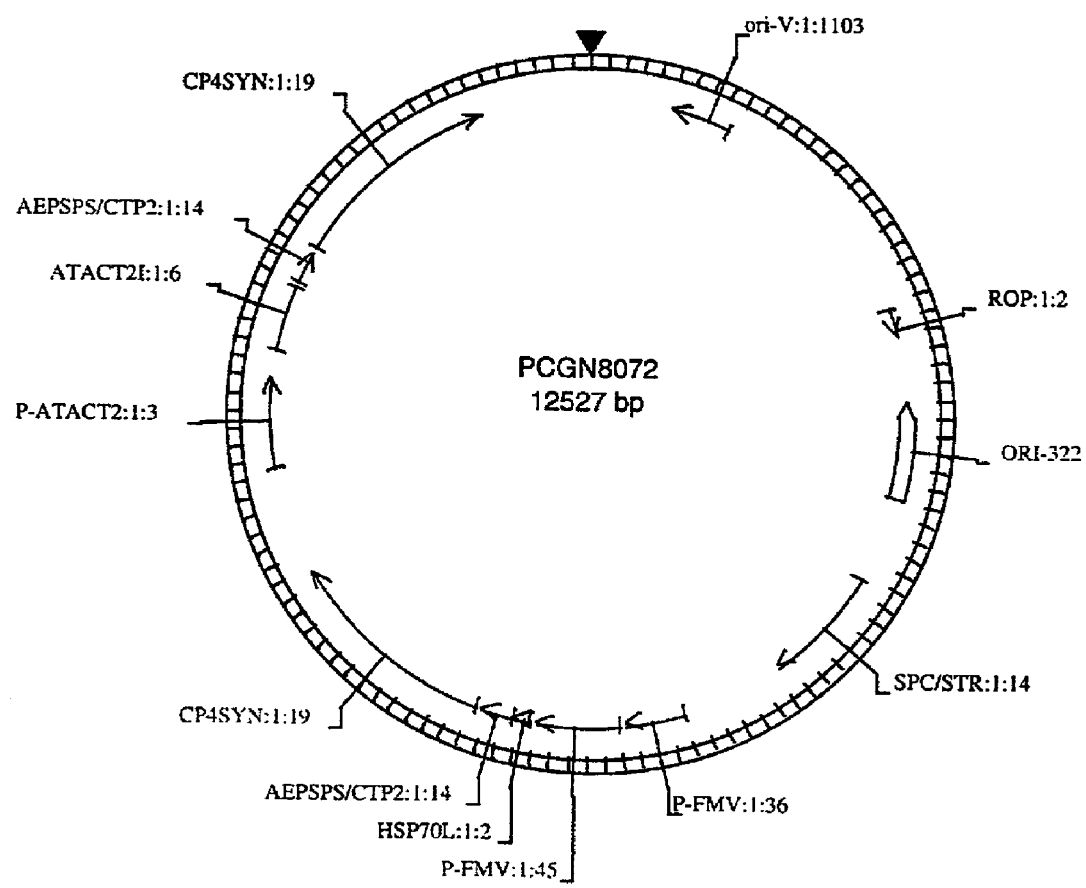
FIG. 6 is a representation of a plasmid map of pCGN8072.
Figure 7:
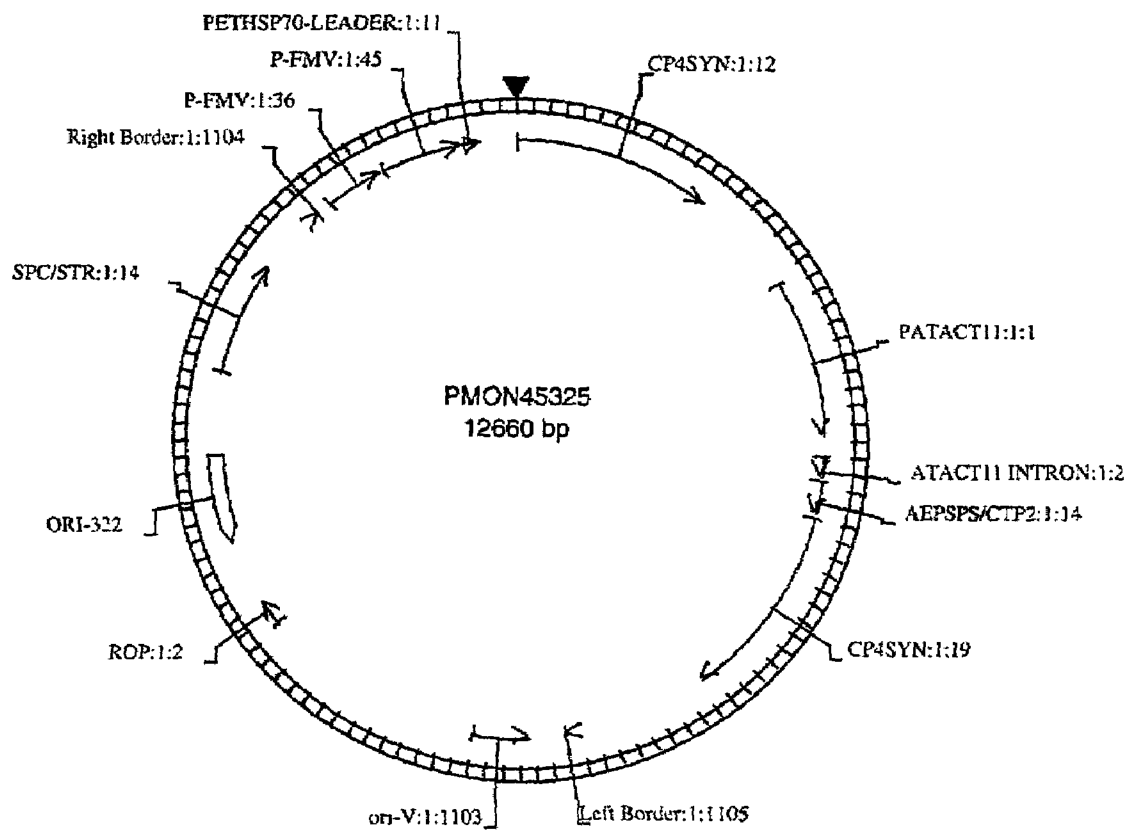
FIG. 7 is a representation of a plasmid map of pMON45325.
Figure 8:
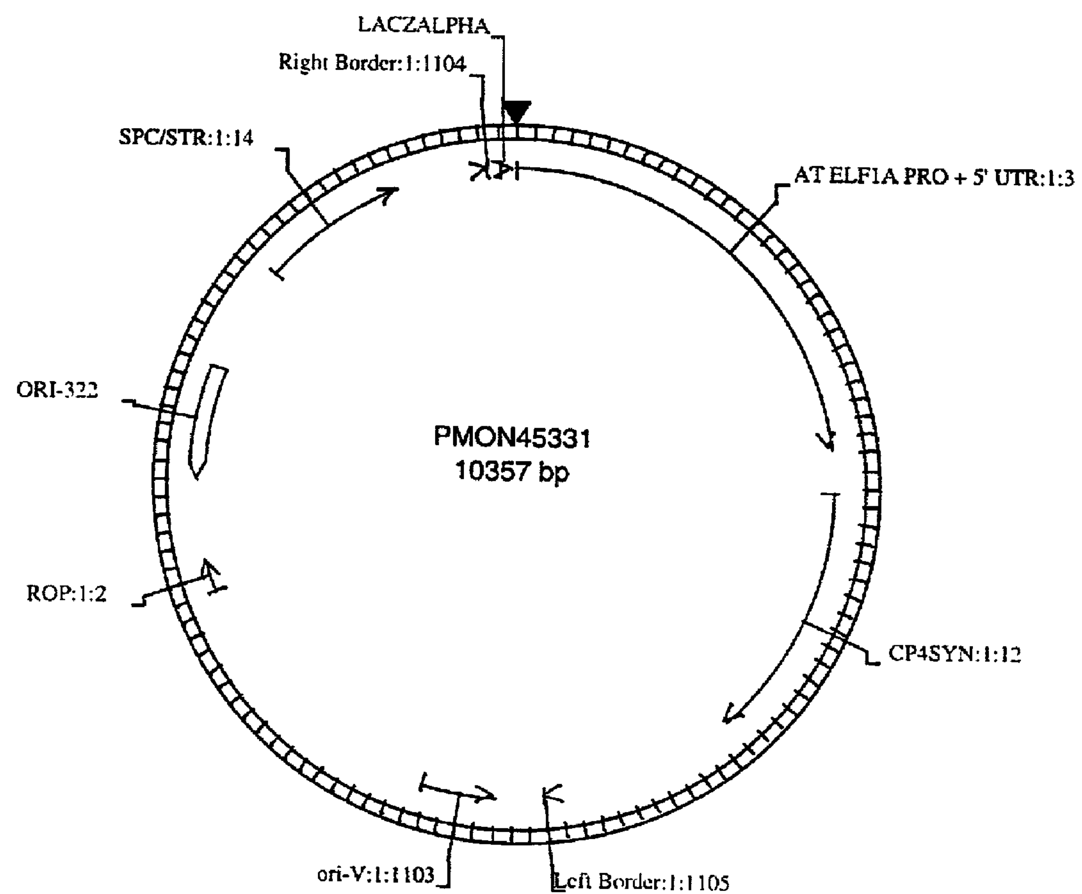
FIG. 8 is a representation of a plasmid map of pMON45331.
Figure 9:
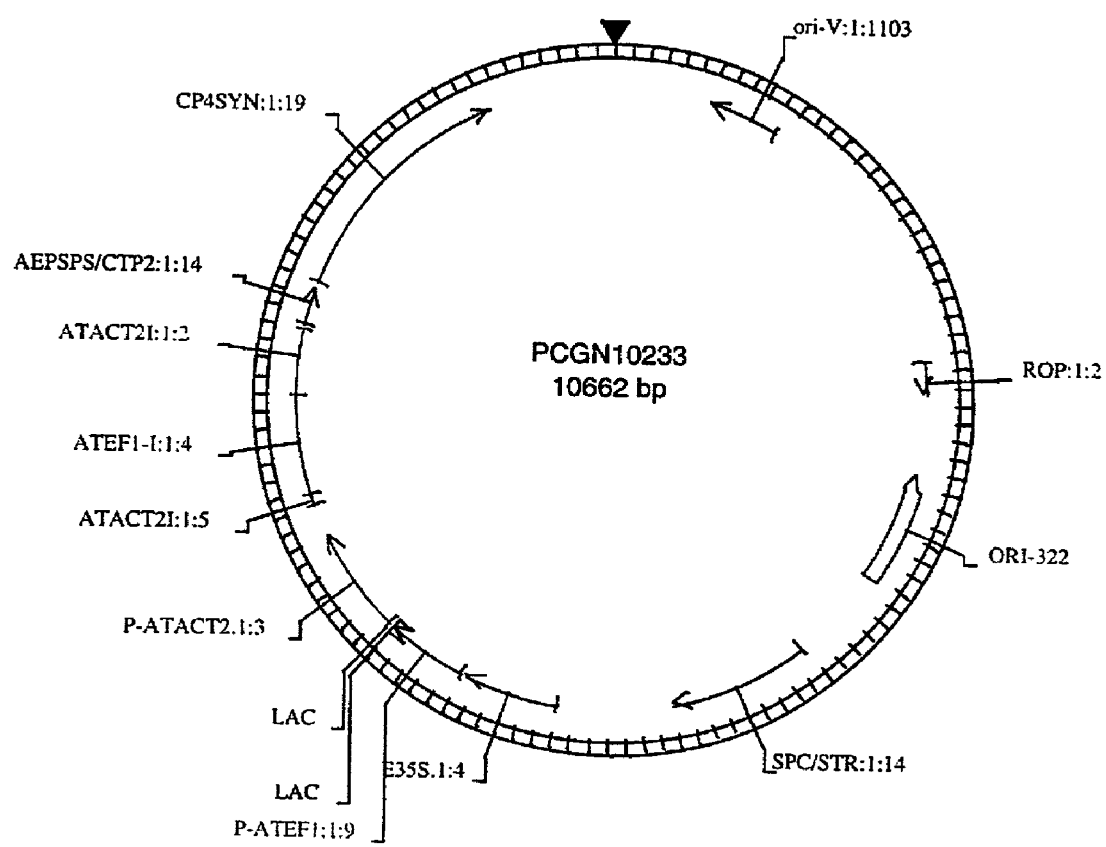
FIG. 9 is a representation of a plasmid map of pCGN10233.
Figure 10:
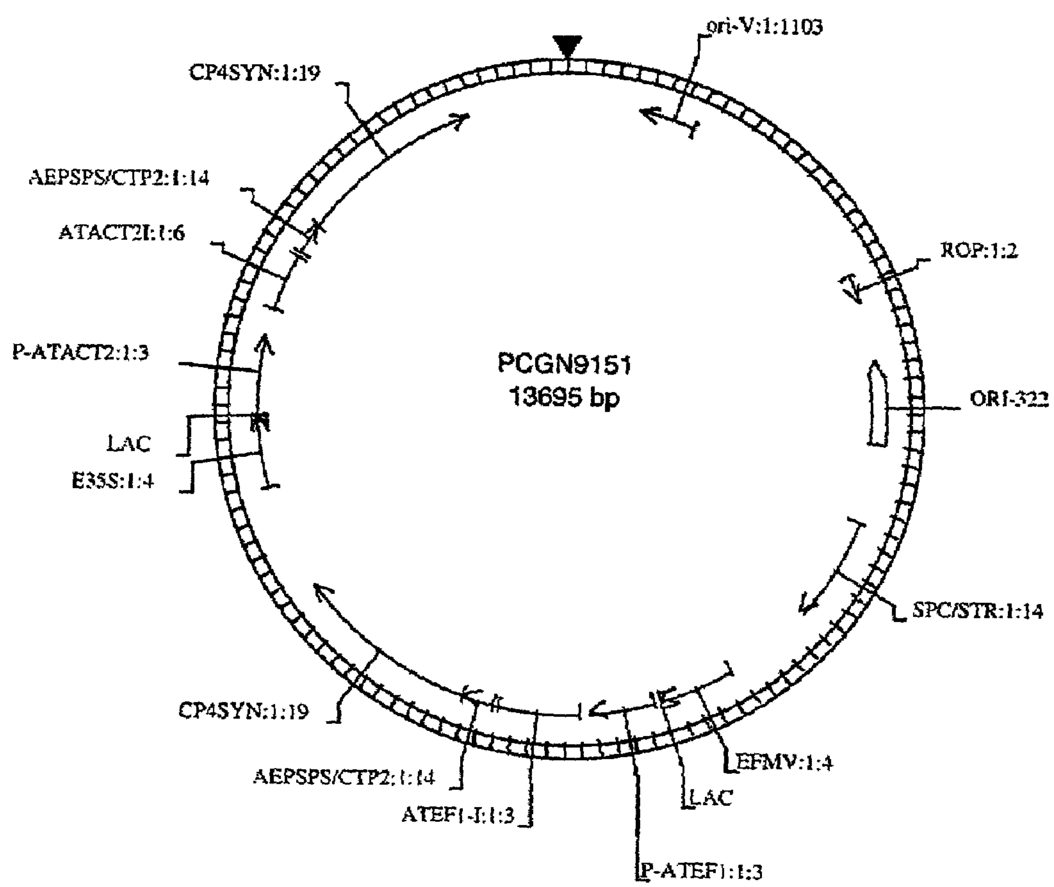
FIG. 10 is a representation of a plasmid map of pCGN9151
Figure 11:
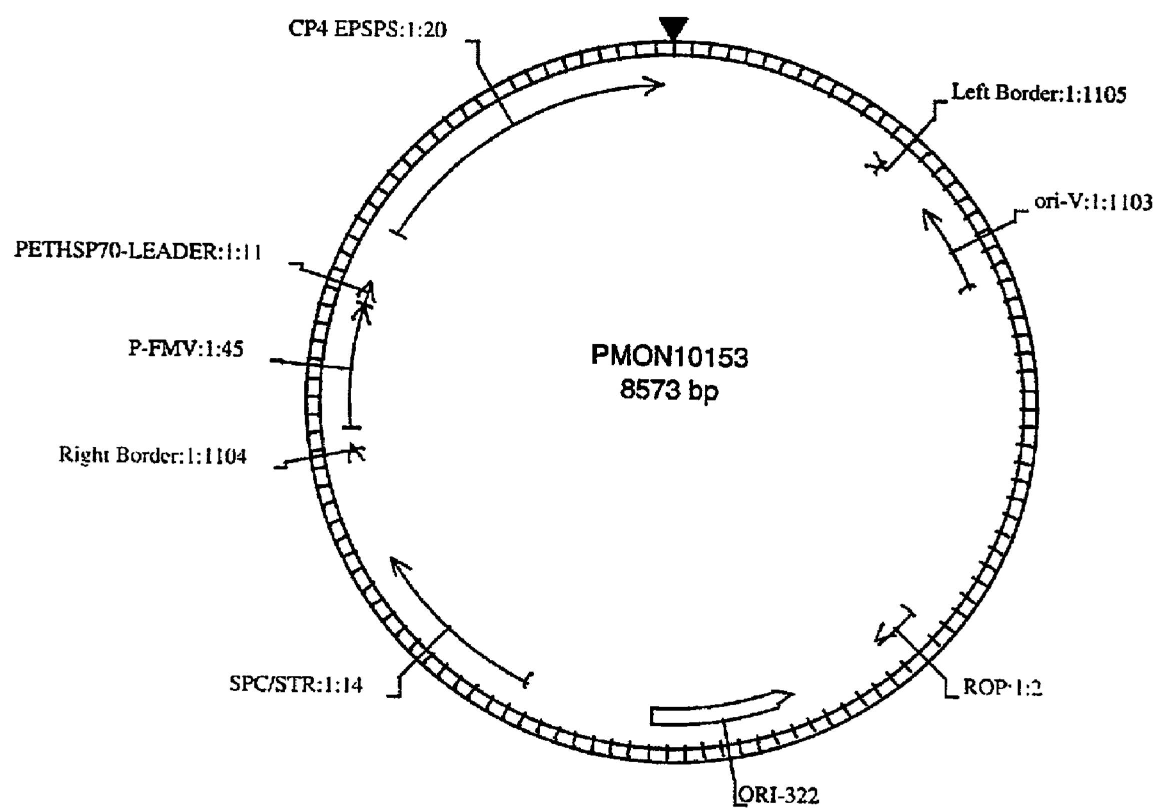
FIG. 11 is a representation of a plasmid map of pMON10153.
Figure 12:
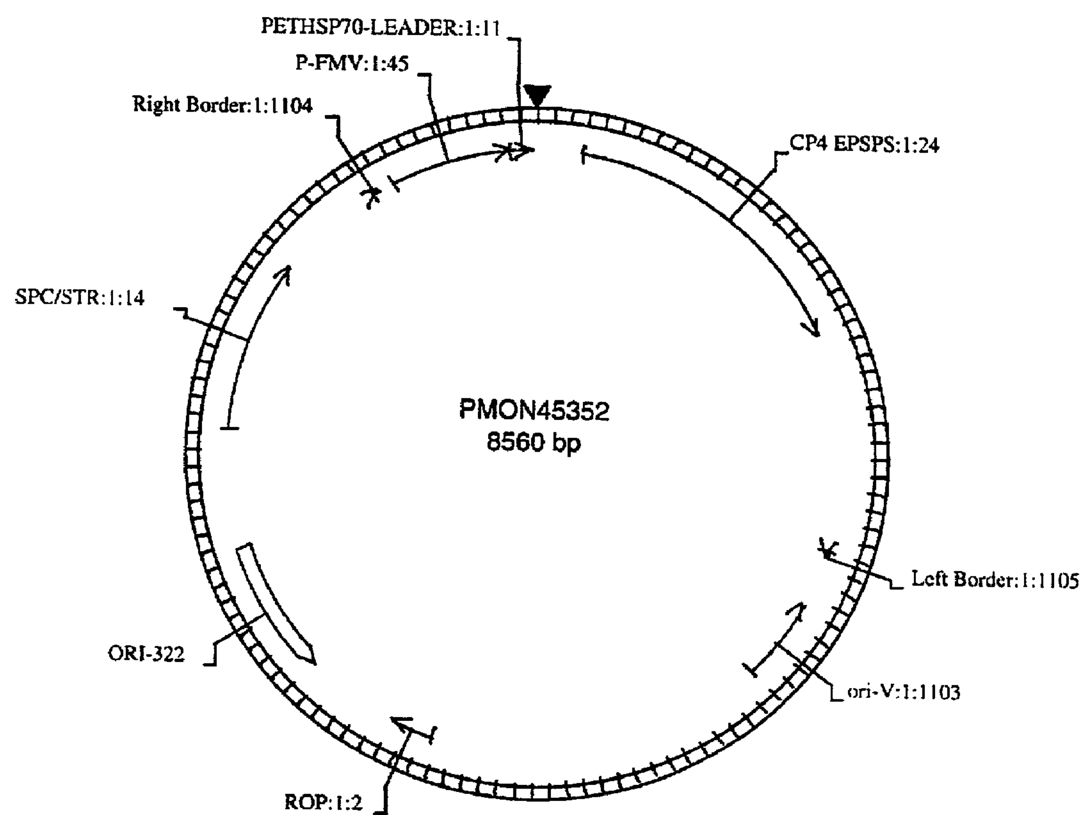
FIG. 12 is a representation of a plasmid map of pMON45352.

The following definitions are provided in order to aid those skilled in the art in understanding the detailed description of the present invention.

"Coding sequence" and "open reading frame" refer to a region of continuous sequential nucleic acid triplets encoding a protein, polypeptide, or peptide sequence.

"Dark or limited lighting conditions" refers to visible light having a maximum intensity from about 0$\mu$ Einsteins $m^{-2}$ $sec^{-1}$ to about 5$\mu$ Einsteins $m^{-2}$ $sec^{-1}$.

"Dicot" or "dicotyledon" refers to plants that produce an embryo with two cotyledons. Examples of dicots include cotton, soybean, sunflower, and peanut.

"Monocot" refers to plants having a single cotyledon (the first leaf of the embryo of seed plants). Examples of monocots include cereals such as maize, rice, wheat, oats, and barley.

"Nucleic acid" refers to deoxyribonucleic acid (DNA) and ribonucleic acid (RNA).

"Osmole" refers to a unit of osmotic pressure. One osmole is the osmotic pressure of a one molar solution of a substance that does not dissociate in water (such as a sugar). Osmotic pressure depends on the total number of dissolved particles, so for a substance that dissociates into two ions, such as ordinary salt (sodium chloride), a one molar solution has an osmotic pressure of 2 osmoles.

"Osmotic pressure" refers to the tendency of a solvent to diffuse across a semi-permeable membrane from an area of low solute concentration to an area of high solute concentration (i.e., from a low osmotic pressure to a high osmotic pressure). A solution with higher solute concentration is said to have a higher osmotic pressure than a solution having a lower concentration of solutes. In practice, most measurements are in milliosmoles (mOsm). Typical values range from 20 mOsm for fresh water through 290 mOsm for typical human blood plasma to 1010 mOsm for salt water from the open ocean.

"Phenotype" refers to traits exhibited by an organism resulting from the interaction of genotype and environment.

"Polyadenylation signal" or "polyA signal" refers to a nucleic acid sequence located 3' to a coding region that promotes the addition of adenylate nucleotides to the 3' end of the mRNA transcribed from the coding region.

"Promoter" or "promoter region" refers to a nucleic acid sequence, usually found upstream (5') to a coding sequence, that controls expression of the coding sequence by controlling production of messenger RNA (mRNA) by providing the recognition site for RNA polymerase and/or other factors necessary for start of transcription at the correct site.

"Recombinant nucleic acid vector" refers to any agent such as a plasmid, cosmid, virus, autonomously replicating sequence, phage, or linear or circular single-stranded or double-stranded DNA or RNA nucleotide segment, derived from any source, capable of genomic integration or autonomous replication, comprising a nucleic acid molecule in which one or more nucleic acid sequences have been linked in a functionally operative manner. Such recombinant nucleic acid constructs or vectors are capable of introducing a 5' regulatory sequence or promoter region and a DNA sequence for a selected gene product into a cell in such a manner that the DNA sequence is transcribed into a functional mRNA that is subsequently translated into a polypeptide or protein. Recombinant nucleic acid constructs or recombinant vectors may be constructed to be capable of expressing antisense RNAs, in order to inhibit translation of a specific RNA of interest.

"Regeneration" refers to the process of growing a plant from a plant cell (e.g., plant protoplast or explant).

"Scion" refers to a detached living portion of a plant, such as a regenerated shoot. Scions may be grafted into another plant.

"Selectable marker" refers to a nucleic acid sequence whose expression confers a phenotype facilitating identification of cells containing the nucleic acid sequence. Selectable markers include those that confer resistance to toxic chemicals (e.g., ampicillin resistance, kanamycin resistance), complement a nutritional deficiency e.g., uracil, histidine, leucine), or impart a visually distinguishing characteristic (e.g., color changes or fluorescence).

"Solute" refers to any substance, organic or inorganic, dissolved in a solvent.

"Transcription" refers to the process of producing an RNA copy from a DNA template.

"Transformation" refers to a process of introducing an exogenous nucleic acid sequence (e.g., a vector, recombinant nucleic acid molecule) into a cell or protoplast in which that exogenous nucleic acid is incorporated into a chromosome or is capable of autonomous replication.

"Transgenic" refers to organisms into which exogenous nucleic acid sequences are integrated.

"Vector" refers to a plasmid, cosmid, bacteriophage, or virus that carries exogenous DNA into a host organism.

The present invention relates to methods of transforming sunflower tissues and regenerating fertile transgenic plants from such tissues. The methods are especially useful when working with sunflower tissues, which have previously been refractory to standard transformation and regeneration protocols.

Preparation of Sunflower Tissue

In general, the invention is suitable for the transformation and regeneration of any *Helianthus* species. The species is preferably *Helianthus annuus* L. The particular strain of *Helianthus annuus* L. preferably is Dekalb 53B, 42B, 34B, 36B, 71B, 53A, 42A, 34A, 36A, 71A, 122R, 161R, HA300A, or HA300B, more preferably is Dekalb 53A, 53B, 42A, 42B, HA300A, or HA300B, and most preferably is HA300B or their F1-hybrids. The sunflower tissue used for the transformation is generally from any source tissue or plant part capable of regenerating shoots, and ultimately, a fertile sunflower plant. The tissue is preferably from a hypocotyl, cotyledon, root, floral tissue, petiole, anther, or leaf. More preferably, the tissue is from a cotyledon, which is derived from any source that can produce a cotyledon such as immature embryos or seeds.

The cotyledon tissue is typically provided from germinated sunflower seeds. The seeds are preferably germinated in a germination medium. Many different forms of media are suitable for the use as germination media. One skilled in the art is familiar with the varieties of media that, when supplemented appropriately, support germination of sunflower seeds. Examples of such media would include, but are not limited to, MS media (Murashige and Skoog, *Physiol. Plant,* 15: 473–497, 1962), Gamborg's media (Gamborg et al., *Exp. Cell Res.,* 50:151, 1968), Woody Plant Media (WPM) (McCown and Lloyd, *Hort. Science* 16:453, 1981), Nitsch and Nitsch media (Nitsch and Nitsch, *Science* 163:85–87, 1969), Schenk and Hildebrandt media (Schenk and Hildebrandt, *Can. J. Bot.* 50:199–204, 1972). Alternatively, sterile distilled water may be supplemented for use as germination media. Any of these culture media, as well as any equivalent forms, fall within the scope of the present invention.

In a preferred embodiment, the germination media is sterile distilled water containing certain additives. The additives may include salts, vitamins, carbohydrates, agar, cytokinins, auxins, antibiotics, anti-mycotics, other plant growth regulators, or combinations thereof. Specific additives to the germination media may include Benlate (E.I. DuPont de Nemour & Co., Wilmington, Del.), Captan (Stauffer Chemical Co., Westport, Conn.), Bravo (SDS Biotech Corp., Plainville, Ohio), carbenicillin, or combinations thereof.

The concentration of the Benlate, Captan, or Bravo in the germination media preferably is between about 0 mg/mL and about 0.5 mg/mL, more preferably is between about 0 mg/mL and about 0.1 mg/mL, even more preferably is between about 0 mg/mL and about 0.05 mg/mL, and most preferably is about 0.03 mg/mL.

The temperature for the germination is preferably between about 15° C. and about 45° C., more preferably between about 20° C. and about 37° C., even more preferably between about 25° C. and about 30° C., and most preferably about 28° C.

The germination is preferably carried out in dark or limited lighting conditions. The dark or limited lighting conditions preferably are between about 0 $\mu Em^{-2} sec^{-1}$ and about 5 $\mu Em^{-2} sec^{-1}$.

The germination is carried out for a time sufficient to produce seedlings. Sufficiently germinated seeds preferably have a seedling measuring in length between about 1 mm and about 30 mm, more preferably between about 5 mm and about 20 mm, and most preferably between about 12 mm and about 18 mm. The time required for sufficient germination preferably is from about 1 day to about 10 days, more preferably from about 1 day to about 5 days, and most preferably is about 2 days.

After germination, seedlings with cotyledons are preferably incubated in the cold. The temperature for this incubation is preferably between about 0° C. and about 20° C., more preferably between about 0° C. and about 10° C., even more preferably between about 0° C. and about 5° C., and most preferably about 4° C.

The period of time in which the sunflower tissue is incubated in the cold is preferably between about 1 hour and about 72 hours, more preferably between about 12 hours and about 60 hours, even more preferably between about 18 hours and about 50 hours, and most preferably between about 20 hours and about 40 hours. A cold incubation period of about 24 hours is appropriate.

The cotyledons from germinated seedlings are preferably transformed within about 60 days of germination, more preferably within about 30 days, even more preferably within about 10 days, and most preferably within about 5 days.

Prior to transformation, the sunflower tissue is typically processed by cutting, tearing, dissecting, slicing, breaking, or otherwise manipulating the tissue. The need for such manipulations will vary depending on the type of tissue selected for the transformation. For instance, cotyledons may be processed by cutting or breaking along one or more horizontal and/or vertical axis. The pieces thus produced may be symmetric or asymmetric relative to each other. Cotyledons are preferably processed along the root-shoot axis ensuring to exclude all pre-formed apical and axillary meristem. This may facilitate the accessibility of the regenerative cells to subsequent steps of the transformation.

The time between the processing of the sunflower tissue and the start of transformation may be an important consideration in the practice of the present invention. The optimal time between the completion of processing and the start of transformation will vary with the particular tissue selected. Cotyledon tissue preferably is subjected to transformation within about 24 hours after processing, more preferably within about 12 hours after processing, even more preferably within about 6 hours after processing, and most preferably within about 2 hours after processing.

Transformation of the Sunflower Tissue

Transformation of the sunflower tissue is generally accomplished using any technique known to those of skill in the art for introducing nucleic acids into cells. The transformation is preferably carried out using bacterial infection, binary bacterial artificial chromosome vectors (BIBAC), direct delivery of nucleic acid (e.g., PEG-mediated transformation), desiccation/inhibition-mediated nucleic acid uptake, electroporation, agitation with silicon carbide fibers, acceleration of particles coated with nucleic acid, or by any other method known to those of skill in the art; more preferably by bacterial infection; even more preferably by *Agrobacterium* infection; and most preferably by *Agrobacterium tumefaciens* infection.

In general, any strain of *Agrobacterium tumefaciens* is suitable for transforming the sunflower tissue. The *Agrobacterium tumefaciens* strain is preferably C58, LBA4404, EHA101, EHA105, EHA109, or ABI, and more preferably ABI.

Preparation of Agrobacteria for inoculation of explants is generally well known to those of skill in the art. For purposes of the present invention, the *Agrobacterium* culture is initiated by inoculating a petri plate containing media such as Luria-Burtani (LB) in agar with selective antibiotics. The concentrations of selective agent as well as the particular selective agent utilized is variable and depends on the host strain. Those of skill in the art are also aware that the timing of culture growth, culture temperature, and concentration of host bacterium may be different for particular transformation systems. The inoculated plate is incubated between about 23° C. and about 30° C., and preferably between about 26° C. and about 28° C. for several days. An individually isolated colony is used to inoculate an LB liquid culture containing selective antibiotics and grown to the proper concentration. The concentration of the culture is typically determined by spectrophotometric measurement of the culture's optical density at 600 nm. The final optical density of the culture (read at 600 nm) is preferably between 0.05 and 4.0. The fresh liquid culture is subsequently used for inoculation of the sunflower tissue.

The *Agrobacterium* typically contains a recombinant nucleic acid vector. Recombinant vectors used to transform plants and methods of making those vectors are described in the art (e.g., U.S. Pat. Nos. 4,971,908, 4,940,835, 4,769,061 and 4,757,011). Recombinant nucleic acid vectors are defined above and generally contain one or more nucleic acid coding sequences of interest under the transcriptional control of 5' and 3' regulatory sequences. Such vectors generally comprise, operatively linked in sequence in the 5' to 3' direction, a promoter sequence that directs the transcription of a downstream heterologous structural nucleic acid sequence in a plant; optionally, a 5' non-translated leader sequence; a nucleic acid sequence that encodes a protein of interest; and a 3' non-translated region that encodes a polyadenylation signal that functions in plant cells to cause the termination of transcription and the addition of polyadenylate nucleotides to the 3" end of the mRNA encoding the protein. Plant transformation vectors also generally contain a selectable marker. Typical 5"–3" regulatory sequences include a transcription initiation start site, a ribosome binding site, an RNA processing signal, a transcription termination site, and/or a polyadenylation signal. Vectors for plant transformation have been reviewed in Rodriguez et al (Vectors: A Survey of Molecular Cloning Vectors and Their Uses, Butterworths, Boston., 1988), Glick et al. (Methods in Plant Molecular Biology and Biotechnology, CRC Press, Boca Raton, Fla., 1993), and Croy (Plant Molecular Biology Labfax, Hames and Rickwood (Eds.), BIOS Scientific Publishers Limited, Oxford, UK., 1993).

The promoter sequences in the recombinant nucleic acid vector can be constitutive or inducible, environmentally- or developmentally-regulated, or cell- or tissue-specific. Often-used constitutive promoters include the CaMV 35S promoter (Odell, J. T. et al., *Nature* 313: 810–812, 1985), the enhanced CaMV 35S promoter, the Figwort Mosaic Virus (FMV) promoter (Richins et al., *Nucleic Acids Res.* 20: 8451–8466, 1987), the mannopine synthase (mas) promoter, the nopaline synthase (nos) promoter, and the octopine synthase (ocs) promoter. Useful inducible promoters include promoters induced by salicylic acid or polyacrylic acids (PR-1, Williams , S. W. et al, *Biotechnology* 10: 540–543, 1992), induced by application of safeners (substituted benzenesulfonamide herbicides, Hershey, H. P. and Stoner, T. D., *Plant Mol. Biol.* 17: 679–690, 1991), heat-shock promoters (Ou-Lee et al., *Proc. Natl. Acad. Sci U.S.A.* 83: 6815–6819, 1986; Ainley et al., *Plant Mol. Biol.* 14: 949–967, 1990), a nitrate-inducible promoter derived from the spinach nitrite reductase gene (Back et al., *Plant Mol. Biol.* 17: 9–18, 1991), hormone-inducible promoters (Yamaguchi-Shinozaki, K. et al., *Plant Mol. Biol.* 15: 905–912, 1990; Kares et al., *Plant Mol. Biol.* 15: 225–236, 1990), and light-inducible promoters associated with the small subunit of RuBP carboxylase and LHCP gene families (Kuhlemeier et al., *Plant Cell* 1: 471, 1989; Feinbaum, R. L. et al., *Mol. Gen. Genet.* 226: 449–456, 1991; Weisshaar, B. et al., *EMBO J.* 10: 1777–1786, 1991; Lam, E. and Chua, N. H., *J. Biol. Chem.* 266: 17131–17135, 1990; Castresana, C. et al., *EMBO J.* 7: 1929–1936, 1988; Schulze-Lefert et al., *EMBO J.* 8: 651, 1989). Examples of useful tissue-specific, developmentally-regulated promoters include the β-conglycinin 7S promoter (Doyle, J. J. et al., *J. Biol. Chem.* 261: 9228–9238, 1986; Slighton and Beachy, *Planta* 172: 356–363, 1987), and seed-specific promoters (Knutzon, D. S. et al., *Proc. Natl. Acad. Sci U.S.A.* 89: 2624–2628, 1992; Bustos, M. M. et al., *EMBO J.* 10: 1469–1479, 1991; Lam and Chua, *Science* 248: 471, 1991; Stayton et al., *Aust. J. Plant. Physiol.* 18: 507, 1991). Plant functional promoters useful for preferential expression in seed plastids include those from plant storage protein genes and from genes involved in fatty acid biosynthesis in oilseeds. Examples of such promoters include the 5" regulatory regions from such genes as napin (Kridl et al., *Seed Sci. Res.* 1: 209–219, 1991), phaseolin, zein, soybean trypsin inhibitor, ACP, stearoyl-ACP desaturase, and oleosin. Seed-specific gene regulation is discussed in EP 0 255 378. Promoter hybrids can also be constructed to enhance transcriptional activity (Comai, L. and Moran, P. M., U.S. Pat. No. 5,106,739, issued Apr. 21, 1992), or to combine desired transcriptional activity and tissue specificity.

In addition to the various regulatory elements, the recombinant vector can also contain a selectable marker. The nucleic acid sequence serving as the selectable marker functions to produce a phenotype in cells that facilitates their identification relative to cells not containing the marker. Useful selectable markers include, but are not limited to, GUS, green fluorescent protein (GFP), luciferase (LUX), antibiotic resistance sequences, and herbicide tolerance sequences.

Characteristics of useful selectable markers for plants have been outlined in a report on the use of microorganisms (Advisory Committee on Novel Foods and Processes, July 1994). These characteristics include stringent selection with minimal contaminating non-transformed tissue, high numbers of independent transformation events without interference in subsequent regenerative steps, application to a large number of species, and availability of an assay to detect the marker. Several antibiotic and herbicide resistance markers satisfy these criteria (Dekeyser et al., *Plant Physiol.,* 90:217–223, 1989; Della-Cioppa et al., Bio/Technology, 5:579–584, 1987). For example, antibiotic resistance to kanamycin (and neomycin, G418, bleomycin) is provided by nptII, hygromycin B by aph IV, and gentamycin by aac3 or aacC4. Resistance to herbicides like glyphosate is also described.

The recombinant nucleic acid vector can contain one or more nucleic acid coding sequences. These sequences may comprise any sequence of nucleic acids but are preferably those that code for proteins, polypeptides, or peptides conferring a desired trait, or phenotype. Examples of such traits include pest tolerance, herbicide tolerance, improvements in yield, nutritional enhancement, environmental or stress tolerance, or any other desirable changes in plant growth, development, and morphology.

Not only can the nucleic acid coding sequences have a variety of biological functions, as described above, they can also originate from diverse sources. The sequences may be derived from the same species of plant, a different species of plant, or a different organism. In addition, the sequence may comprise a synthetic nucleic acid or a naturally occurring sequence that has been manipulated using molecular biological techniques.

The *Agrobacterium*-mediated transformation is typically carried out in an infiltration media. Many different forms of media are suitable for the infiltration media. One skilled in the art is familiar with the varieties of media that, when supplemented appropriately, support the transformation of plant cells. Examples of such media would include but are not limited to MS media, Gamborg's media, Woody Plant Media (WPM), Nitsch and Nitsch media, Schenk and Hildebrandt media, or variations thereof. Any of these culture media, as well as any equivalent forms, fall within the scope of the present invention. In a preferred embodiment, the infiltration media is MS media and typically contains additives. The additives generally comprise salts, vitamins, carbohydrates, amino acids, agar, cytokinins, auxins, other plant growth regulators, antibiotics, antimycotics, or combinations thereof. The infiltration media most preferably comprises low levels of cytokinins and carbohydrates and does not contain auxins.

The infiltration media preferably contains between about 0 mL/L and about 25 mL/L of B-5 vitamin stock (see Table 1), more preferably between about 0 mL/L and about 10 mL/L, even more preferably between about 0 mL/L and about 5 mL/L, and most preferably about 5 mL/L.

The infiltration media preferably contains SILWET L-77 (Monsanto Co., St. Louis, Mo.). The concentration of the SILWET L-77 in the infiltration media is preferably between about 0 μL/L and about 1000 μL/L, more preferably between about 0 μL/L and about 500 μL/L, even more preferably between about 100 μL/L and about 250 μL/L, and most preferably 200 μL/L.

The infiltration media also preferably contains acetosyringone (Aldrich Chemical Co., Milwaukee, Wis.). The concentration of the acetosyringone in the infiltration media is preferably between about 0 μM and about 1000 μM, more preferably between about 0 μM and about 500 μM, even more preferably between about 100 μM and about 250 μM, and most preferably 200 μM.

The infiltration media preferably contains a source of carbohydrates. The carbohydrate is preferably glucose, sucrose, fructose, maltose, mannose, mannitol, xylose, or combinations thereof, and most preferably is sucrose. The optimal concentration of the carbohydrate source in the infiltration media is preferably between about 0% (w/v) and about 20% (w/v), more preferably between about 0% (w/v) and about 15% (w/v), even more preferably between about 3% (w/v) and about 10% (w/v), and most preferably about 5% (w/v).

The infiltration media also preferably contains 6-benzylaminopurine. The concentration of 6-benzylaminopurine in the infiltration media is preferably between about 0 μg/mL and about 1000 μg/mL, more preferably between about 0 μg/mL and about 100 μg/mL, even more preferably between about 0 μp g/mL and about 10 μg/mL, even more preferably between about 0 μg/mL and about 1 μg/mL, and most preferably about 0.1 μg/mL.

The infiltration media also preferably contains 2-[N-morpholino]-ethanesulfonic acid (MES). The concentration of 2-[N-morpholino]-ethanesulfonic acid in the infiltration media is preferably between about 0 mg/mL and about 10 mg/mL, more preferably between about 0 mg/mL and about 5 mg/mL, even more preferably between about 0 mg/mL and about 1 mg/mL, and most preferably about 0.5 mg/mL.

The pH of the infiltration media is preferably between about 2 and about 12, more preferably between about 4 and about 8, even more preferably between about 5 and about 7, and most preferably about 5.7.

The transformation is preferably carried out under low 18/6 light. The low 18/6 light is preferably less than about 60 $\mu Em^{-2}$ $sec^{-1}$, more preferably less than about 45 $\mu Em^{-2}$ $sec^{-1}$, and most preferably is less than about 30 $\mu Em^{-2}$ $sec^{-1}$.

The optimal temperature for the transformation is preferably between about 15° C. and about 40° C., more preferably between about 18° C. and about 37° C., even more preferably between about 19° C. and about 28° C., and most preferably about 23° C. The duration of the transformation process varies. The transformation preferably is performed in about 1 day to about 7 days, more preferably in about 1 day to about 5 days, and most preferably in about 2 days to about 4 days.

Post-Transformation Delay Culture

Following transformation, the sunflower tissue is typically cultured in a delay medium. The delay media is typically optimized to limit the growth of the *Agrobacterium* while allowing for the continued growth of transformed cells in the cotyledon tissue. Many different forms of media are suitable for the delay culture. One skilled in the art is familiar with the varieties of media which, when supplemented appropriately, support plant tissue growth and development while limiting bacterial growth. Examples of such media would include but are not limited to MS media, Gamborg's media, Woody Plant Media (WPM), Nitsch and Nitsch media, Schenk and Hildebrandt media, or variations thereof. Any of these culture media, as well as any equivalent forms, fall within the scope of the present invention. In a preferred embodiment, the delay media is MS media and typically contains additives. The additives generally comprise salts, vitamins, carbohydrates, amino acids, agar, cytokinins, auxins, other plant growth regulators, antibiotics, anti-mycotics, or combinations thereof.

The delay media preferably possesses a high osmotic pressure. Osmotic pressure is defined above. The osmotic pressure of the media is preferably between about 20 mOsm and about 1100 mOsm, more preferably between about 100 mOsm and about 900 mOsm, and most preferably between about 200 mOsm and about 750 mOsm.

The high osmolarity of the delay media is typically provided by any solute compatible with the growth of plant cells. Suitable solutes include, but are not limited to, organic salts, inorganic salts, and carbohydrates. The solute preferably is a carbohydrate, more preferably is glucose, sucrose, mannitol, fructose, maltose, mannose, or xylose, and most preferably is sucrose.

The optimal concentration of the solute in the delay media varies with the particular solute selected. The concentration of the carbohydrate in the delay media is preferably between about 5% (w/v) and about 30% (w/v), more preferably between about 7.5% (w/v) and about 20% (w/v), even more preferably between about 10% (w/v) and about 15% (w/v), and most preferably about 12% (w/v).

The delay media can also contain 6-benzylaminopurine. The concentration of 6-benzylaminopurine in the delay media is preferably between about 0 μg/mL and about 1000 μg/mL, more preferably between about 0 μg/mL and about 100 μg/mL, even more preferably between about 0 μg/mL and about 10 μg/mL, even more preferably between about 0 μg/mL and about 1 μg/mL, and most preferably about 0.1 μg/mL.

The pH of the delay media is preferably between about 2 and about 12, more preferably between about 4 and about 8, even more preferably between about 5 and about 7, and most preferably about 5.8.

The temperature of the delay culture is preferably between about 15° C. and about 40° C., more preferably between about 20° C. and about 37 ° C., even more preferably between about 22° C. and about 28° C., and most preferably about 23° C.

The transformed plant tissue is preferably incubated in the delay media from about 1 day to about 20 days, more preferably from about 4 days to about 14 days, and most preferably from about 4 days to about 10 days.

Selection of Transformed Tissue

Following the delay culture, the sunflower tissue is typically transferred to a culture optimized for the selection of transformed cells or tissues. Many different forms of media are suitable for this selection culture. One of ordinary skill in the art is familiar with the varieties of media that, when supplemented appropriately, support plant tissue growth and development. Examples of such media include, but are not limited to, MS media, Gamborg's media, Woody Plant Media (WPM), Nitsch and Nitsch media, Schenk and Hildebrandt media, or modifications thereof. Any of these culture media, as well as any equivalent forms, fall within the scope of the present invention.

In a preferred embodiment, the culture media is based on MS media and typically contains additives. The additives may comprise salts, vitamins, carbohydrates, amino acids, agar, cytokinins, auxins, antibiotics, antimycotics, other plant growth regulators, or combinations thereof.

The selective media typically contains one or more antibiotics to prevent the growth of the *Agrobacterium*. The range of inhibitory antibiotics will vary, depending on the *Agrobacterium* strain used. Those of skill in the art are familiar with the antibiotics used to inhibit *Agrobacterium* remaining in the culture while allowing growth of the transgenic tissue. Examples of *Agrobacterium* inhibitory antibiotics useful for practice of this invention may include carbenicillin and cefotaxime.

The concentration of carbenicillin in the selection media preferably is between about 0 mg/mL and about 10 mg/mL, more is preferably between about 0 mg/mL and about 5 mg/mL, even more preferably between about 0 mg/mL and about 1 mg/mL, and most preferably about 0.4 mg/mL.

The concentration of cefotaxime in the selection media is preferably between about 0 mg/mL and about 10 mg/mL, more preferably between about 0 mg/mL and about 5 mg/mL, even more preferably between about 0 mg/L and about 1 mg/L, and most preferably about 0.1 mg/mL.

The selection media also preferably contains 6-benzylaminopurine. The concentration of 6-benzylaminopurine in the selection media is preferably between about 0 μg/mL and about 1000 μg/mL, more preferably between about 0 μg/mL and about 100 μg/mL, even more preferably between about 0 μg/mL and about 10 μg/mL, even more preferably between about 0 μg/mL and about 1 μg/mL, and most preferably about 0.1 μg/mL.

The selection media can also contain Benomyl. The concentration of Benomyl in the selection media is preferably between about 0 mg/mL and about 1.0 mg/mL, more preferably between about 0 mg/mL and about 0.5 mg/mL, even more preferably between about 0 mg/mL and about 0.1 mg/mL, and most preferably about 0.05 mg/mL.

In addition to antibiotics to inhibit the growth of the Agrobacteria, a selection agent is typically added to limit the growth of non-transformed plant cells. The selection agent is a substance that is toxic to non-transformed cells but not to the transformed cells. The transformed cells generally incorporate and produce a selectable marker at a level suitable to confer resistance to the selection agent. The selection agent is generally any selection agent compatible with the present invention. The selection may be carried out in a plurality of steps involving several different cultures. The tissues are typically transferred between selection cultures with each culture containing a varying concentration of the selection agent. Alternatively, the concentration of the selection agent may be held constant through each of the cultures.

The selection is preferably performed by transferring the transformed tissue through two or more different selection cultures. The first culture preferably contains a selection medium having a low concentration of selective agent; the second culture preferably contains a high concentration of selective agent in the media. In this manner, a low selective pressure is followed by a high selective pressure. Additional selective cultures can be provided that preferably contain low selection pressure (e.g., low-high-low selection).

The amount of selection agent in the low and high selection media will vary with the particular selective agent used. The selection agent is preferably kanamycin or paromomycin, at a concentration up to about 150 mg/L, or glyphosate, at a concentration up to about 2.5 mM. One skilled in the art will appreciate that the concentration of the selective agent will vary with the culture media employed as well as the particular selective agent utilized.

The low concentration of glyphosate in the selection media (used in the first and third selection cultures) is preferably between about 0 mM and about 0.2 mM, more preferably between about 0 mM and about 0.1 mM, and most preferably between about 0.04 mM and about 0.06 mM.

The high concentration of glyphosate in the selection media (used in the second selection culture) is preferably between about 0.05 mM and about 1 mM, more preferably between about 0.05 mM and about 0.5 mM, even more preferably between about 0.05 mM and about 0.25 mM, and most preferably between about 0.07 mM and about 0.13 mM.

The length of time permitted for each step of the selection will vary depending on the particular selective agent used. The duration of each step of the selection is preferably from about 1 day to about 14 days.

Typically during or after the second selection step, transgenic shoots may form. The selection cultures are monitored for the induction of such transgenic shoots. Any tissues forming transgenic shoots are typically transferred to a shoot elongation medium. Alternatively, the transgenic shoots may be maintained in the selection cultures until all of the steps of the selection are complete and then transferred to a shoot elongation medium.

The selection media preferably contains a source of carbohydrates. The carbohydrate preferably is glucose, sucrose, fructose, maltose, mannose, mannitol, or xylose, and most preferably sucrose. The optimal concentration of the carbohydrate in the selection media varies with the particular carbohydrates selected. The concentration of the carbohydrate in the selection media is preferably between about 0% (w/v) and about 20% (w/v), more preferably between about 0% (w/v) and about 10% (w/v), even more preferably between about 0% (w/v) and about 5% (w/v), and most preferably about 1% (w/v). Thus, the selection media will have a low osmotic pressure.

Elongation of Transgenic Shoots

Transgenic shoots identified in the selection cultures are typically transferred to culture containing a shoot elongation medium. Many different forms of media are suitable for shoot elongation. One of ordinary skill in the art is familiar with the varieties of media that, when supplemented appropriately, support such plant shoot growth and development. Examples of such media include, but are not limited to, MS media, Gamborg's media, Woody Plant Media (WPM), Nitsch and Nitsch media, Schenk and Hildebrandt media, or modifications thereof. Any of these culture media, as well as any equivalent forms, fall within the scope of the present invention.

In a preferred embodiment, the shoot elongation media is based on MS media and typically contains additives. The additives generally comprise salts, vitamins, carbohydrates, amino acids, agar, cytokinins, auxins, antibiotics, anti-mycotics, other plant growth regulators, or combinations thereof.

The shoot elongation media preferably contains an antibiotic. The antibiotic can be any antibiotic compatible with the present invention. The antibiotic is preferably carbenicillin and/or cefotaxime.

The concentration of carbenicillin in the shoot elongation media is preferably between about 0 mg/mL and about 10 mg/mL, more preferably between about 0 mg/mL and about 5 mg/mL, even more preferably between about 0 mg/mL and about 1 mg/mL, and most preferably between about 0 mg/L and about 0.4 mg/mL.

The concentration of cefotaxime in the shoot elongation media is preferably between about 0 mg/mL and about 10 mg/mL, more preferably between about 0 mg/mL and about 5 mg/mL, even more preferably between about 0 mg/L and about 1 mg/L, and most preferably between about 0 mg/mL and about 0.1 mg/mL.

The shoot elongation media can also contain Benomyl. The concentration of Benomyl in the shoot elongation media is preferably between about 0 mg/mL and about 0.5 mg/mL, more preferably between about 0 mg/mL and about 0.1 mg/mL, even more preferably between about 0 mg/mL and about 0.05 mg/mL, and most preferably about 0.025 mg/mL.

The shoot elongation media preferably contains a source of carbohydrates. The carbohydrate preferably is glucose, sucrose, fructose, maltose, mannose, mannitol, or xylose, and most preferably sucrose. The optimal concentration of the carbohydrate in the shoot elongation media varies with the particular carbohydrates selected. The concentration of the carbohydrate in the shoot elongation media is preferably between about 0% (w/v) and about 20% (w/v), more preferably between about 0% (w/v) and about 10% (w/v), even more preferably between about 0% (w/v) and about 5% (w/v), and most preferably about 1% (w/v). Thus, the shoot elongation media has a low osmotic pressure.

The shoot elongation media can further contain gibberellic acid ($GA_3$). The gibberellic acid in the shoot elongation media is preferably between about 0 $\mu$g/mL and about 100 $\mu$g/mL, more preferably between about 0 $\mu$g/mL and about 10 $\mu$g/mL, even more preferably between about 0 $\mu$g/mL to about 5 $\mu$g/mL, and most preferably about 0.5 to 1 $\mu$g/mL.

Selective pressure can be maintained in the shoot elongation media by adding a selection agent to the media, in a low concentration, as described above.

The pH of the shoot elongation media is preferably between about 2 and about 12, more preferably between about 4 and about 8, even more preferably between about 5 and about 7, and most preferably between about 5.5 and 6.0. The shoot elongation culture is preferably maintained at a temperature between about 15° C. and about 40° C., more preferably between about 20° C. and about 37° C., and most preferably between about 22° C. and about 30° C.

The transformed sunflower tissues can be maintained in the shoot elongation media for about 1 day to about 14 days. However, the duration of these cultures may be extended if additional shoot elongation is needed.

The shoot elongation cultures are typically maintained under high 18/6 light. The intensity of the high 18/6 light is preferably between about 30 $\mu Em^{-2}$ $sec^{-1}$ and about 200

$\mu Em^{-2}$ $sec^{-1}$, more preferably between about 50 $\mu Em^{-2}$ $sec^{-1}$ and about 150 $\mu Em^{-2}$ $sec^{-1}$, and most preferably about 100 $\mu Em^{-2}$ $sec^{-1}$.

As transgenic shoots grow and develop, they are typically transferred to a second shoot elongation medium (also referred to as a pre-rooting medium). The second elongation media, with respect to the types of additives and the concentrations of those additives in the media, is described above. Additional additives can include glutamine and Phloridzin (Sigma Company, St. Louis, Mo.).

The glutamine in the second shoot induction media preferably is between about 0 mg/mL and about 1 mg/mL, more preferably is between about 0 mg/mL and about 0.5 mg/mL, and most preferably is about 0.2 mg/mL.

The Phloridzin in the second shoot induction media preferably is between about 0 mg/mL and about 0.5 mg/mL, more preferably is between about 0 mg/mL and about 0.1 mg/mL, even more preferably is between about 0 mg/mL and about 0.05 mg/mL, and most preferably is about 0.015 mg/mL.

Regeneration of Transgenic Plants

After the period of elongation, the elongated transgenic shoots are typically either planted in soil or grafted onto non-transgenic or transgenic sunflower plants. For instance, scions can be grafted onto stock plants and transferred to a greenhouse. This R(0) generation is then allowed to grow, develop, flower, and produce seeds. Alternatively, the shoots can be directly rooted on rooting media and allowed to grow, develop, flower, and produce seeds. In either case, the seeds or plants thus produced may be tested to confirm the presence of the nucleic acid sequence transferred via *Agrobacterium* during the transformation. These seeds may then be used to produce subsequent generations of transgenic plants.

The transgenic plant tissues, seeds, and/or plants can be analyzed for the presence of the DNA sequence introduced by the transformation. There are a variety of molecular and biochemical assays for detecting the DNA sequence or the encoded protein that are well known in the art. These assays include PCR, western blotting, immunohistochemistry, ELISA, northern blotting, and southern blotting. Once the presence of the nucleic acid sequence or the encoded protein is confirmed, these independent transgenic sunflower lines can be further tested for agronomic efficacy under growth chamber, greenhouse, or field conditions.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Sterilization of Sunflower Seeds with Chlorine Gas

Petri dishes (25 mm in diameter) were filled with approximately 20 grams of sunflower seeds and covered with lids. These petri dishes were then transferred to a plastic autoclavable dessicator and placed in a fume hood at room temperature. A sterile glass beaker containing 200 mL of bleach (5.25% sodium hypochlorite) was placed in the center of the desiccator. Approximately 2 mL of concentrated hydrochloric acid (12.1 M) was then added to the beaker containing the bleach. The desiccator was then covered with a lid, forming a tight seal. The desiccator was connected to a vacuum line and a vacuum of about 20 in. Hg was formed. The seeds were incubated in this fashion for about 16 hours to 24 hours. After this incubation, the vacuum was released, the desiccator lid removed, and gases allowed to escape into the fume hood. The petri dishes were transferred from the desiccator to a sterile laminar flow hood. The petri dish lids were then removed and the seeds were allowed to air for about 10 minutes. The seeds were then ready for use.

Example 2

Germination of Seeds

Sterilized seeds were placed in a sterile flask. About 50 mL of germination media was then added to each flask. This germination medium was made by thoroughly mixing 1 gram of Benlate, 1 gram of Captan, and 1 gram of Bravo into 100 mL of sterile distilled water to make a stock solution. From this stock, 3 mL were added to one liter of sterile distilled water to complete the germination medium. The flasks were then covered and agitated in a shaker (approximately 100 rpm) at 28° C. in the dark. After about 24 hours of shaking, the germination media was removed from the flasks and about 75 mL of fresh germination media was added to each flask. The flasks were then placed back on the shaker (approximately 100 rpm) at 28° C. in the dark for about 20 more hours. Seeds were monitored for the formation of seedlings. Seedlings measuring approximately 15 mm in length were considered ready for use.

TABLE 1

MEDIA COMPOSITIONS

| NAME | COMPOSITION (per liter) |
|---|---|
| LBSCK (plates) | 10 grams NaCl; 5 grams Yeast Extract; 10 grams Tryptone; 15 grams Agar; 50 mg Kanamycin; 25 mg Choloramphenicol; 100 mg Spectinomycin |
| LBSCK (liquid media) | 10 grams NaCl; 5 grams Yeast Extract; 10 grams Tryptone; 50 mg Kanamycin; 25 mg Choloramphenicol; 100 mg Spectinomycin |
| YEP | 10 grams Peptone; 10 grams Yeast Extract; 5 grams NaCl |
| Infiltration (inoculation/co-culture) Media | 2.2 grams MS Salts (major & micro), 5 mL of 100X B5 Vitamins, 50 grams Sucrose; 0.5 grams MES, 0.1 mg BAP; pH 5.7. 200 $\mu$M acetosyringone; 200 $\mu$L/L SILWET L-77 (in inoculum only) at the time of use |

TABLE 1-continued

MEDIA COMPOSITIONS

| NAME | COMPOSITION (per liter) |
|---|---|
| Delay Media | 4.31 grams MS Salts (major and micro); 120 grams Sucrose; 1 mL MS Vita (of 1000X MS vitamins); 8 grams agar; 0.1 mL BAP (1 mg/mL); pH 5.8 |
| Selection Media | 4.31 grams MS Salts (major and micro); 10 grams Sucrose; 1 mL of 1000X MS Vits ; 0.05 grams Benomyl; 8 grams agar 0 1 ml. BAP (1 mg/mL); 10 mL Carbenicillin (40 mg/mL); 2 mL Cefotaxime (50 mg/mL); (Glyphosate(0.5 M) is added to the final concentrations indicated in the text |
| Shoot Elongation Media | 4.31 grams MS Salts (major and micro); 10 grams Sucrose; 1 mL of 1000X MS Vits; 0.025 grams Benomyl; 7 grams agar 5 mL Carbenicillin (40 mg/mL); 1 mL Cefotaxime (50 mg/mL); 1 mL Giberellic acid (1 mg/mL) |
| Shoot Development Medium | 2.2 grams MS salts (major and micro); 20 grams Sucrose; 1 ml of 100X MS Vitamin stock; 0.5 grams GA3; 0.05 grams Benomyl; 9 grams agar 5 mL Carbenicillin (of 40 mg/mL stock); 1 mL Cefotaxime (of 50 mg/mL stock) |
| B5 Vitamin Stock (=100X) | 1 gram inositol; 0.1 gram nicotinic acid, 0 1 gram pysidoxine-HCl; 1 gram thiamine-HCl |

Example 3

Preparation of *Agrobacterium tumefaciens*

From a stock culture of *Agrobacterium tumefaciens* harboring a nucleic acid vector of interest, 20 mL glass tubes containing about 2 mL of LBSPCK (see Table 1) were inoculated. The inoculated cultures were placed in a shaker (160 rpm) at 26° C. under limited light conditions. After shaking for about 16 hours, this culture was used to inoculate a 250 mL flask containing fresh LB media (Table 1) at a 1:10 ratio. This culture was placed on a shaker (160 rpm) at 26° C. under limited light conditions and incubated overnight. The cultures were grown to an optical density (at 600 nm) of about 2.5 to 3.0. Cultures reaching this density were transferred to sterile tubes and subjected to centrifugation at 3000 rpm, 2619 g (will vary for the head used and for different centrifuges), for 10 minutes to pellet the bacteria. The media was removed and the pellet of bacteria was re-suspended in infiltration media to yield a final optical density of about 2.0.

Several different *Agrobacterium* stock cultures, each harboring a different nucleic acid vector, were prepared. A number of these vectors are listed in Table 2. Each of these vectors has been used to successfully transform sunflower cotyledons and regenerate subsequent transgenic plants.

TABLE 2

Selected Nucleic Acid Vectors Conferring Glyphosate Resistance

| Vector Name | Components |
|---|---|
| pWRG4750 | FMV CP4 syn, 35S GUS, NOS npt II |
| pMON20998 | eFMV CP4 syn |
| pMON20999 | FMV CP4 syn |
| pMON45332 | PP3 – CP4 + eFMV CP4 |
| pMON10156 | eFMV CP4 syn |
| pCGN8072 | eFMV CP4 syn + PP1 CP4 syn |
| pMON45325 | eFMV CP4 syn + PP2 CP4 syn |
| pMON45331 | PP3 CP4syn |

FMV is the full length transcript promoter from the figwort mosaic virus; CP4 syn is a synthetic EPSPS gene that confers glyphosate resistance; 35S is the 35S promoter from Cauliflower Mosaic Virus (CaMV); gus is the gene for β-galactosidase; NOS is the nos 3" transcription terminator; nptII is the nopaline synthase gene that confers kanamycin resistance; PP1 is the *Arabidopsis* Actin 2 promoter; PP2 is the *Arabidopsis* Actin 11 promoter; and PP3 is the *Arabidopsis* elongation factor 1A promoter.

Example 4

Preparation of Germinated Sunflower Tissue

In a laminar flow hood, germinated seeds were rinsed twice with 100 mL of sterile distilled water. The water was poured onto the germinated seeds and removed each time by repeatedly decanting it with a 25-mL pipette. After the final draining of the water, the flasks containing the germinated seeds were covered and incubated at 4° C. for about 1 to 10 days.

On the day of the transformation, the seed coats were removed from the germinated seeds by pushing out the seedlings. These uncoated seedlings were placed in sterile distilled water in a petri dish until the seed coats had been removed from all of the germinated seeds. The petri dish was then drained, covered, sealed with parafilm, and placed at 4° C. until use (approximately 1 to 16 hours).

Example 5

Transformation of Sunflower Cotyledons

Just prior to transformation, cotyledons were removed from the seedlings and placed in 6-well plates (approximately 25 cotyledons in each well). The cotyledons were broken off from the rest of the seedlings at the root/shoot axis ensuring to exclude all preformed apical and axillary meristem. Only unblemished cotyledons were used. To each well, 7 mL of *Agrobacterium tumefaciens* (re-suspended in infiltration media plus 200 μM acetosyringone and 200 μL/L SILWET L-77 at an O.D. of ~2.0, as in Example 3) were added. The cotyledons were soaked, covered, and incubated for one hour under the light of a laminar flow hood. Plates containing experimental controls (cotyledons receiving infiltration media with no *Agrobacterium tumefaciens*) were also prepared.

After soaking the cotyledons for about an hour, the cotyledons were removed and placed adaxial surface up in plates containing filter paper wetted with 5 mL of infiltration media. The cotyledons were then incubated at 23° C. under low 18/6 light for about 48 to 72 hours. Several different lines of sunflower seeds were assessed for transformation ability using the presently disclosed methods. The results, which are indicated in Table 3, demonstrate that the transformation of sunflower cotyledons may be applied to a variety of sunflower strains. Furthermore, these successfully transformed sunflower strains were further capable of regenerating into fertile transgenic plants.

TABLE 3

Transformation and Regeneration from Sunflower Cotyledons

| Strain | Agrobacterium Transformation | Regeneration of Plants |
|---|---|---|
| USDA HA300B | yes | yes |
| Dekalb 42B | yes | yes |
| Dekalb 53B | yes | yes |
| Asgrow H565 | yes | yes |

Example 6

Post-Transformation Delay Culture

After co-culture with the *Agrobacterium*, the cotyledons were transferred to plates containing Delay media (see Table 1). The cotyledons were pushed into the media with adaxial surfaces facing up. The plates were covered, sealed with parafilm, and incubated at 23° C. under low 18/6 light for about 7 days.

Example 7

Selection of Transformed Cotyledon Tissue

After the post-transformation delay, the transformed cotyledons were transferred through a series of selection cultures containing low-high-low concentrations of selective agent. The cotyledons were first placed in Selection media (see Table 1) containing 0.05 mM glyphosate for about 10 days. Plates were incubated at 23° C., low light, and 18/6 hour photoperiod. The cotyledons were then transferred to a second selection culture containing Selection media+0.1 mM glyphosate for about 2 additional weeks. Finally, the cotyledons were placed in a third selection culture containing Selection media+0.05 mM glyphosate for about 7 to 14 days. In addition to glyphosate, several other selection agents were tested (Table 4). The results demonstrate that a variety of different selection agents are compatible with the present invention.

TABLE 4

Assessment of Selection Agents

| Selective agent | GUS Positive/Total cotyledons assayed* | GUS Positive Shoots |
|---|---|---|
| Glyphosate | 63/80 | 7 |
| Paromomycin 25 -> 50 -> 25 mg/L | 15/30 | 7 |
| Kanamycin 50 mg/L | 59/64 | 16 |

*Destructive GUS assays were performed at different stages of the experiments to determine *Agrobacterium* transfection and the effectiveness of selective agents.

Example 8

Induction of Transgenic Shoots

The cotyledons in the selection cultures were monitored for the formation of transgenic shoots. The transgenic shoots that formed were transferred to shoot elongation media (see Table 1) and incubated at 25° C. under 18/6 high light for about 10 days. The frequency with which transgenic shoots formed is provided in Table 5. Results of several independent transformations with various nucleic acid vectors are indicated.

TABLE 5

Frequency of Transgenic Shoot Formation

| Vector Construct | Total No Cotyledons | No of Cotyledons with Shoots | Frequency of Transgenic Shoots |
|---|---|---|---|
| pWRG4750 | 2036 | 174 | 8.5% |
| pMON20998 | 2520 | 139 | 5.5% |
| pMON20999 | 1723 | 114 | 6.6% |
| pCGN8072 | 1613 | 59 | 3.7% |
| pMON45325 | 2862 | 193 | 6.7% |
| pMON45331 | 8274 | 354 | 4.3% |
| pMON45332 | 2186 | 150 | 6.9% |
| pCGN10233 | 1520 | 68 | 4.5% |
| pCGN9151 | 1480 | 49 | 3.3% |
| pMON10153 | 3442 | 127 | 3.7% |
| pMON45352 | 8775 | 419 | 4.8% |

These results clearly show that the transformed cotyledons are fully capable of developing transgenic shoots.

Example 9

Regeneration of Transgenic Sunflower Plants

The transgenic shoots were then transferred to shoot development media (see Table 1) to promote the formation of roots. As roots formed they were potted in a sterile vessel in vermiculite. Sufficient shoot development media was added to saturate the vermiculite. Any excess media (after about 10 minutes) was poured off.

The potted shoots were allowed to grow and develop into plants under standard greenhouse conditions.

The ability to regenerate transgenic plants after transformation with several different recombinant vectors was assessed. The results, which are indicated in Table 6, demonstrate that methods of transformation and regeneration are not only successful, but may be used with a variety of nucleic acid vectors.

TABLE 6

Frequency of Regenerated Transgenic Sunflower Plants

| Plasmic/Marker (used for the transformation) | Number of Cotyledons Inoculated | Number of Transgenic Plants in Greenhouse | Frequency of Transgenic Plants |
|---|---|---|---|
| **pWRG4750/ 35s GUS | 2936 | 21 | 0.7% |
| pMON20998/ eFMVCP4 | 2520 | 9 | 0.4% |
| pMON20999/ FMVCP4 | 1723 | 8 | 0 5% |
| pCGN8072 | 1613 | 6 | 04% |
| pMON45325 | 2862 | 13 | 0.5% |
| pMON45331 | 8274 | 34 | 0.4% |

TABLE 6-continued

Frequency of Regenerated Transgenic Sunflower Plants

| Plasmic/Marker (used for the transformation) | Number of Cotyledons Inoculated | Number of Transgenic Plants in Greenhouse | Frequency of Transgenic Plants |
|---|---|---|---|
| pMON45332 | 2186 | 56 | 2 6% |
| pMON10153 | 3442 | 47 | 1.4% |
| pMON45352 | 8775 | 106 | 1.2% |

**plasmid for experimentation only not all shoots grafted.

Regenerative ability was also assessed for several different sunflower varieties (see Table 3). The results demonstrated that the present methods are successful in both transforming sunflower cotyledons from a number of different strains and regenerating plants from the transformed cotyledons.

Transgenic shoots that did not form roots were grafted onto non-transgenic or transgenic stock plants. Three- to four-week-old plants, with two to four sets of expanded leaves, were used as stock or recipient plants (plants with roots). Apical shoot meristem, along with new and expanding leaves, was removed, with a scalpel, by making a horizontal stem cut about 1.5 to 5 cm from the shoot top. Lower part of the scion was shaved vertically at an angle to provide a wedge of about 0.5 to 2 cm. A vertical cut of about 1 to 3 cm length is made in top part of the stem just outside of the pith and scion shoot is inserted into this cut. Attempt is made to align cortex and vascular bundles of stock and scion. The area, where stock and scion overlap, is first wrapped with parafilm and then string is tied tightly around it to provide a good connection of stock and scion. A plastic clothespin may be put around it to provide additional pressure to bring stock and scion areas together. The plants are covered with a transparent plastic bag that is tied with twist at the lower part. The plants are allowed to adapt in the lab at low temperature of about 22° C. to 24° C., in low light, for 18 to 24 hours. Plants were then transferred to 12 to 16 hour photoperiod, white fluorescent light and a temperature of 24 to 26° C. The plastic bag is removed as scion shoots start to grow in 5 to 10 days. The frequency with which transgenic shoots were successfully grafted is provided in Table 7.

TABLE 7

Survival of Transgenic Grafts Transformed with Different Vectors

| Vector Construct | No Grafts | No Surviving Grafts | Frequency of Survival |
|---|---|---|---|
| pWRG4750 | 51 | 21 | 41% |
| pMON20998 | 56 | 9 | 16% |
| pMON20999 | 44 | 3 | 18% |
| pMON45325 | 44 | 13 | 30% |
| pCGN8072 | 21 | 6 | 29% |
| pMON45331 | 76 | 34 | 45% |
| pMON45332 | 100 | 56 | 56% |
| pMON10153 | 93 | 47 | 51% |
| pMON45352 | 182 | 106 | 58% |

As the data indicates, high levels of graft survival were achieved. This demonstrates that transgenic shoots that did not form roots are still competent for regeneration into intact plants via the grafting process. Furthermore, the grafting may be performed with transgenic shoots containing a wide variety of nucleic acid vectors.

Example 10

Assessment of the Glyphosate Tolerance of Transgenic Sunflower Plants

Transgenic R1 sunflower plants (from strain HA300B), transformed with pWRG4750, were transformed and regenerated as described in Examples 5–9 and tested in greenhouse. About 5000 R2 seeds of two independent transformants, SFB193 and SFB216, were planted. Some plants were sprayed with Glyphosate at V-4 and V-8 leaf stages at 0 and 32 oz/acre level. For the other plants, glyphosate treatment rates, at V4 stage were 0-, 32-, or 64 oz./acre. The sunflower plants were assessed for resistance to glyphosate. An excellent vegetative tolerance was achieved at 32 and 64 oz/acre levels of glyphosate spray at both V4 and V8 stages of plant development.

Greenhouse tolerance of transgenic plants to glyphosate spray results are summarized in Table 8. In addition, the glyphosate-treated transgenic plants were scored for normal head development. These results are summarized in Table 9.

TABLE 8

Tolerance of Transgenic Sunflowers to Various Levels of Glyphosate spray in greenhouse at about v6 to v10 leaf stage of plant growth.

| Strain | 0 oz./acre | 32 oz./acre | 64 oz./acre | 96 oz./acre | 128 oz./acre |
|---|---|---|---|---|---|
| HA300B (Control) | Foliar and Reproductive Tolerance | No Tolerance | No Tolerance | No Tolerance | No Tolerance |
| SFB193 | Foliar and Reproductive Tolerance | Foliar and Reproductive Tolerance | Foliar and Reproductive Tolerance | Foliar Tolerance | Foliar Tolerance |
| SFB216 | Foliar and Reproductive Tolerance | Foliar and Reproductive Tolerance | Foliar and Reproductive Tolerance | Foliar Tolerance | Foliar Tolerance |

SFB193 and SFB216 are independent transformants from experiments 193 and 216.

TABLE 9

Normal Sunflower Heads After Treatment With Glyphosate

| Strain | 0 oz./acre | 32 oz./acre | 64 oz./acre | 96 oz./acre | 128 oz./acre |
|---|---|---|---|---|---|
| HA300B (Control) | 100% | 0% | 0% | 0% | 0% |
| SFB193 | 67% | 56% | 79% | 50% | 25% |
| SFB216 | 94% | 70% | 32% | 14% | 0% |

These data clearly show that the transgenic sunflower plants tested have superior foliar glyphosate resistance at all treatment levels when compared with the non-transgenic control. Furthermore, at the 32- and 64 oz./acre levels the transgenic plants were able to reach reproductive maturity. In addition, a high percentage of the glyphosate treated plants developed normal heads.

All of the compositions and methods disclosed and claimed herein can be made and executed without undue experimentation in light of the present disclosure. Although the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. All such similar substitutes and modifications apparent to those skilled in the art are deemed to be within the spirit, scope and concept of the invention.

What is claimed is:

1. A method for producing transformed sunflower cotyledons comprising:

obtaining a cotyledon from a germinated sunflower seedling;

incubating the cotyledon at a temperature between about 0° C. and about 10° C.; contacting the cotyledon with a culture of *Agrobacterium* in an infiltration media comprising 6-benzylaminopurine, one or more cytokinins, and one or more carbohydrates; culturing the *Agrobacterium*-contacted cotyledon in a first media to produce transformed cotyledon tissue, wherein the first media has a high osmotic pressure and said first media comprises at least one carbohydrate selected from the group consisting of glucose, sucrose, mannitol, fructose, maltose, mannose, or xylose at a concentration of about 5% (w/v) to about 30% (w/v);

inducing shoot growth from the transformed cotyledon tissue in a second media, wherein the second media has a low osmotic pressure; and incubating the transformed cotyledon tissue thus produced in a selection media comprising at least one selection agent.

2. The method of claim 1, wherein the high osmotic pressure of the first media is between about 200 mOsm and about 750 mOsm.

3. The method of claim 1, further comprising processing said cotyledon along the axis between the root and shoot prior to contacting the cotyledon with the culture of *Agrobacterium.*

4. The method of claim 1, wherein the carbohydrate in the infiltration media is sucrose.

5. The method of claim 1, wherein the concentration of the carbohydrate in the infiltration media is less than about 5% (w/v).

6. The method of claim 1, wherein the cytokinin in the infiltration media is 6-benzylaminopurine.

7. The method of claim 1, wherein the concentration of the cytokinin in the infiltration media is less than about 0.5 μg/mL.

8. The method of claim 1, wherein the selection media comprises glyphos ate, paromomycin, G418, or kanamycin.

9. The method of claim 8, wherein the concentration of the glyphosate in the selection media is from about 0 mM to about 0.5 mM.

10. The method of claim 1, wherein the incubating the transformed cotyledon tissue comprises sequentially incubating in a first, second, and third selection media.

11. The method of claim 10, wherein the first selection media comprises from about 0 mM to about 0.06 mM glyphosate, the second selection media comprises from about 0.075 mM to about 0.25 mM glyphosate, and the third selection media comprises from about 0 mM to about 0.06 mM glyphosate.

12. The method of claim 1, further comprising the step of culturing the transformed cotyledon tissue to produce transgenic shoots.

13. The method of claim 12, further comprising the step of culturing trausgenic shoots to produce a transgenic sunflower plant.

14. The method of claim 13, further comprising the step of growing the transgenic sunflower plant to produce transgenic sunflower seeds.

15. The method of claim 1, wherein the *Agrobacterium* comprises a recombinant nucleic acid vector comprising operatively linked in the 5" to 3" direction:

a promoter that functions in a sunflower cell to direct transcription of a structural nucleic acid sequence;

a structural nucleic acid sequence;

a 3" transcriptional termination signal; and a 3" polyadenylation signal.

16. The method of claim 15, wherein the nucleic acid vector further comprises a selectable marker.

17. The method of claim 16, wherein the selectable marker is a kanamycin resistance marker, a hygromycin resistance marker, or a herbicide resistance marker.

18. The method of claim 15, wherein the promoter is seed specific, tissue specific, constitutive, or inducible.

19. The method of claim 15, wherein the promoter is the nopaline synthase (NOS), octopine synthase (OCS), mannopine synthase (mas), cauliflower mosaic virus 19S and 35S (CaMV19S, CaMV35S), enhanced CaMV (eCaMV), ribulose 1,5-bisphosphate carboxylase (ssRUBISCO), figwort mosaic virus (FMV), CaMV derived AS4, tobacco RB7, wheat POX1, tobacco EIF-4, lectin protein (Le1), or rice RC2 promoter.

20. The method of claim 15, wherein the structural nucleic acid sequence is a synthetic, plant, fungal, or bacterial structural nucleic acid sequence.

* * * * *